(12) United States Patent
Ye

(10) Patent No.: US 8,501,928 B2
(45) Date of Patent: Aug. 6, 2013

(54) CHIMERIC PROMOTER MOLECULES FOR GENE EXPRESSION IN PROKARYOTES

(75) Inventor: Xudong Ye, Madison, WI (US)

(73) Assignee: Monsanto Technology LLC, St. Louis, MO (US)

(*) Notice: Subject to any disclaimer, the term of this patent is extended or adjusted under 35 U.S.C. 154(b) by 929 days.

(21) Appl. No.: 12/401,112

(22) Filed: Mar. 10, 2009

(65) Prior Publication Data
US 2009/0239228 A1 Sep. 24, 2009

Related U.S. Application Data

(60) Provisional application No. 61/035,255, filed on Mar. 10, 2008.

(51) Int. Cl.
*C07H 21/04* (2006.01)
*C12N 15/11* (2006.01)

(52) U.S. Cl.
USPC ........................................ 536/24.1; 536/23.1

(58) Field of Classification Search
None
See application file for complete search history.

(56) References Cited

U.S. PATENT DOCUMENTS

| 5,716,819 A * | 2/1998 | Chatterjee | 435/194 |
| 2005/0044593 A1* | 2/2005 | Cox et al. | 800/288 |
| 2012/0077264 A1* | 3/2012 | Martinell et al. | 435/320.1 |

FOREIGN PATENT DOCUMENTS

| WO | WO 99/46394 | 9/1999 |
| WO | WO 2008/112645 | 9/2008 |

OTHER PUBLICATIONS da Silva Neto et al. Site-directed gene disruption in *Xylella fastidiosa*. FEMS Microbiol Lett. Apr. 23, 2002;210(1):105-10.*
Laursen et al. Initiation of protein synthesis in bacteria. Microbiol Mol Biol Rev. Mar. 2005;69(1):101-23.*
Sandvang D. Novel streptomycin and spectinomycin resistance gene as a gene cassette within a class 1 integron isolated from *Escherichia coli*. Antimicrob Agents Chemother. Dec. 1999;43(12):3036-8.*
GenBank accession No. AF252864, 2002.*
Benfey et al., "The CaMV 35S enhancer contains at least two domains which can confer different developmental and tissue-specific expression patterns," *EMBO J.*, 8(8):2195-2202, 1989.
Cho et al., "Regulation of root hair initiation and expansin gene expression in *Arabidopsis*," *The Plant Cell*, 14:3237-3253, 2002.
GenBank Accession No. AE008688, dated Oct. 30, 2007.
GenBank Accession No. AE008689, dated Oct. 30, 2007.
GenBank Accession No. AE008980, dated May 28, 2004.
GenBank Accession No. AE009201, dated May 28, 2004.
GenBank Accession No. AE009324, dated May 28, 2004.
GenBank Accession No. AE009348, dated May 28, 2004.
GenBank Accession No. CP000738, dated Jun. 29, 2007.
GenBank Accession No. NC_003047, dated May 1, 2009.
GenBank Accession No. NC_007761, dated May 1, 2009.
GenBank Accession No. NC_008380, dated Apr. 25, 2009.
Kim et al., "A 20 nucleotide upstream element is essential for the nopaline synthase (nos) promoter activity," *Plant Molecular Biology*, 24:105-117, 1994.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Welsch et al., "Structural and functional characterization of the phytoene synthase promoter from *Arabidopsis thaliana*," *Planta*, 216:523-534, 2003.
Gustafson at al., "Regulation of sinorhizobium meliloti 1021 rrnA-reporter gene fusions in response to cold shock," *Can. J. Microbiol.*, 48(9):821-830, 2002.
Park et al., "Hererologous expression of cholesterol oxidase in *Bifidobacterium longum* under the control of 16S rRNA gene promoter of bifidobacteria," *Biotechnol Lett*, 30:165-172, 2008.

* cited by examiner

*Primary Examiner* — Michele K Joike
(74) *Attorney, Agent, or Firm* — Dentons US LLP; Erin Robert

(57) ABSTRACT

The present invention provides regulatory polynucleotide molecules isolated from a 16S rDNA for enhanced expression of heterologous genes. The invention further discloses compositions, polynucleotide constructs, transformed host cells containing the regulatory polynucleotide sequences, and methods for preparing and using the same.

5 Claims, 12 Drawing Sheets

FIG. 1

```
C58_operon3   --------------------GATTATTTGACTGCTTTGAAGTGGTCTGTTTTTTGACAATTGAATATGAG    50
C58_operon4   GCTTTTAGCTTTTGGGGTTTGATTTTGTGACTGCATTG-AGCGGTCTGTTTTTTGACAATTGAATATGAG    69
C58_operon1   -------------------------------------GAAGTGGTCTGTTTTTTGACAATTGAATATGAG   33
C58_operon2   ---------TTCGGAGTTTGATTATTTGACTGCTTTGAAGTGGTCTGTTTTTTGACAATTGAATATGAG    60

Consensus     ....................gatt.t.tgactgc.ttGaAGtGGTCTGTTTTTTGACAATTGAATATGAG    70
                                                      ↑

C58_operon3   AAGAAAGAGAAACGTGGGCGGCGAAGCTTGCGGGTCTGGAGCAATTCAGGTCCTAGTGAATAGACTTTG   120
C58_operon4   AAGAAAGAGAAACGTGGGCGGCGAAGCTTGCGGGACCTGGAGAGATTTGGGTCCTAGTGAATAGACTTTG   139
C58_operon1   AAGAAAGAGAAACGTGGGCGGCGAAGCTTGCGGGACCTGGAGAGATTTGGGTCCTAGTGAATAGACTTTG   103
C58_operon2   AAGAAAGAGAAACGTGGGCGGCGAAGCTTGCGGGACCTGGAGAGATTTGGGTCCTAGTGAATAGACTTTG   130

Consensus     AAGAAAGAGAAACGTGGGCGGCGAAGCTTGCGGGacCTGGAGagATTtgGGTCCTAGTGAATAGACTTTG   140

C58_operon3   ACGGTCACGTTTTAATGAGACAACACCAATTTCGCGGGCAGCGATGTTCGTTGAGATTGATGTGAGTTCT   190
C58_operon4   ACGGTCACGTTTTAATGAGACAACACCAATTTCGCGAGCAGAGATGTTTGTTGAGATTGATGTGAGTTCT   209
C58_operon1   ACGGTCACGTTTTAATGAGACAACACCAATTTCGCGAGCAGAGATGCTTGTTGAGATTGATGTGAGTTCT   173
C58_operon2   ACGGTCACGTTTTAATGAGACAACACCAATTTCGCGAGCAGAGATGCTTGTTGAGATTGATGTGAGTTCT   200

Consensus     ACGGTCACGTTTTAATGAGACAACACCAATTTCGCGaGCAGaGATG.TtGTTGAGATTGATGTGAGTTCT   210

C58_operon3   CGTCGATTCAGAATAACGTGACAATAGTCAATGATTGAATTCTCAACTTGAGAGTTTGATCCTGGCTCAG   260
C58_operon4   CGTCGATTCAGAATAACGTGACAATAGTCAATGATTGAATTCTCAACTTGAGAGTTTGATCCTGGCTCAG   279
C58_operon1   CGTCGATTCAGAATAACGTGACAATAGTCAATGATTGAATTCTCAACTTGAGAGTTTGATCCTGGCTCAG   243
C58_operon2   CGTCGATTCAGAATAACGTGACAATAGTCAATGATTGAATTCTCAACTTGAGAGTTTGATCCTGGCTCAG   270

Consensus     CGTCGATTCAGAATAACGTGACAATAGTCAATGATTGAATTCTCAACTTGAGAGTTTGATCCTGGCTCAG   280
                                                      ↑
```

FIG. 2

Agrobacterium-specific cis enhancer upstream of *Hin*dIII site (italicized)
5'GGTCTGTTTTTTGACAATTGAATATGAGAAGAAAGAGAAACGTGGGCG
GCG*AAGCTT*GCGGGACCTGGAGAGATTTGGGTCCTAGTGAATAGACTTT
GACGGTCACGTTTTAATGAGACAACACCAATTTCGCGAGCAGAGATGCT
TGTTGAGATTGATGTGAG<u>TTCTCGT</u>CGATTCAGAATAACGTGACA<u>ATAGT</u>
         -35                    -10
<u>CA</u>ATGATTGAA(GG<u>AG</u>AAACAAaGcc)ATG 3'
P-rrn      virE RBS    initiation codon

FIG. 3

5'GCGGGACCTGGAGAGATTTGGGTCCTAGTGAATAGACTTTGACGGTCACGT
TTTAATGAGACAACACCAATTTCGCGAGCAGAGATGCTTGTTGAGATTGATG
TGAGTTCTCGTCGATTCAGAATAACGTGACAATAGTCAATGATTGAAGGAGA
AACAAaGcC ATG 3'

FIG. 4

5'
GTCTGTTTTTTGACAATTGAATATGAGAAGAAAGAGAAACGTGGGCGGCG<u>AA</u>
<u>GCTAGCTT</u>GCGGGACCTGGAGAGATTTGGGTCCTAGTGAATAGACTTTGACG
GTCACGTTTTAATGAGACAACACCAATTTCGCGAGCAGAGATGCTTGTTGAG
ATTGATGTGAGTTCTCGTCGATTCAGAATAACGTGACAATAGTCAATGATTGA
AGGAGAAACAAaGccATG 3'

CHIMERIC PROMOTER MOLECULES FOR GENE EXPRESSION IN PROKARYOTES

CROSS REFERENCE TO RELATED APPLICATIONS

This application claims the priority of U.S. Provisional Application Ser. No. 61/035,255 filed Mar. 10, 2008, the entire disclosure of which is incorporated herein by reference.

INCORPORATION-BY-REFERENCE OF SEQUENCE LISTING IN COMPUTER READABLE FORM

The Sequence Listing, which is a part of the present disclosure, includes a computer readable form 18.9 KB file entitled "MONS196US_ST25.txt" comprising nucleotide sequences of the present invention. The subject matter of the Sequence Listing is incorporated herein by reference in its entirety.

BACKGROUND OF THE INVENTION

1. Field of the Invention

The present invention relates to the field of molecular biology and genetic engineering, and polynucleic acid molecules useful for gene expression in prokaryotes. Specifically, the present invention discloses chimeric polynucleic acid molecules comprising promoter activity in bacterial cells. The invention further discloses DNA constructs and bacterial cells comprising the polynucleic acid molecules, and methods of producing and using the same.

2. Description of Related Art

One of the goals of genetic engineering is to produce organisms with desirable characteristics or traits. The proper expression of a desirable transgene in a transgenic organism is one way to achieve this goal. Elements having gene regulatory activity, i.e. regulatory elements such as promoters, leaders, and transcription termination regions, are non-coding polynucleotide molecules that play an integral part in the overall expression of genes in living cells. Regulatory elements that function in prokaryotes are therefore useful for modifying their phenotypes through the methods of genetic engineering.

While previous work has provided a number of regulatory elements useful to affect gene expression in transgenic bacteria, there is still a great need for novel regulatory elements with beneficial expression characteristics. Many previously identified regulatory elements fail to provide the patterns or levels of expression required to fully realize the benefits of expression of selected genes in transgenic bacteria. One example of this is the need for regulatory elements capable of driving strong gene expression in different types of bacteria.

A promoter is a key element for directing gene expression in a cell. The transcription machinery is assembled and transcription is initiated from the promoter DNA molecule. Transcription factors influence the strength of a transcript from a promoter molecule. Accordingly, regions within the promoter molecule function to enhance or repress transcription.

The genetic enhancement of bacteria provides significant benefits to society. For example, bacteria may be enhanced with a transgene to provide desirable biosynthetic, commercial, chemical, insecticidal, industrial, nutritional, or pharmaceutical properties. Despite the availability of many molecular tools, however, the genetic modification of bacteria is often constrained by an insufficient expression of the engineered transgene.

High level gene expression requires a strong 5' regulatory sequence (promoter) and may also be affected by sequences found 3' to a coding sequence. Currently only a limited number of strong promoters are available from prokaryotes. Thus, there is a need for additional promoters that are useful for expressing genes, especially single copy genes in a single or low copy vector.

SUMMARY OF THE INVENTION

In one aspect, the invention provides a polynucleotide molecule comprising a 16S rDNA promoter molecule operably linked to a nucleic acid comprising a heterologous ribosomal binding site, wherein the polynucleotide molecule has promoter activity. The 16S rDNA promoter molecule may be isolated from a prokaryote. In specific embodiments, the 16S rDNA promoter molecule comprises a nucleic acid sequence selected from the group consisting of: a) a nucleic acid sequence comprising SEQ ID NO:1, SEQ ID NO:2, SEQ ID NO:3, or SEQ ID NO:4, or any of SEQ ID NOs:22-37; b) a nucleic acid sequence comprising at least 65% sequence identity to SEQ ID NO:1, SEQ ID NO:2, SEQ ID NO:3, or SEQ ID NO:4, or any of SEQ ID NOs:22-37, wherein the nucleic acid sequence comprises promoter activity; and c) a fragment of the nucleic acid sequence of SEQ ID NO:1, SEQ ID NO:2, SEQ ID NO:3, or SEQ ID NO:4, or any of SEQ ID NOs:22-37, wherein the fragment has promoter activity. In further embodiments, the prokaryote is a bacterium, and may be a member of the Rhizobiales further including, for example, *Rhizobium* spp., *Sinorhizobium* spp., *Mesorhizobium* spp., *Phyllobacterium* spp., *Ochrobactrum* spp., and *Bradyrhizobium* spp. In still further embodiments, the ribosomal binding site may be isolated from the *Agrobacterium* virE operon.

In another aspect, a polynucleotide molecule of the invention may be defined as comprising a sequence selected from the group consisting of: a) a nucleic acid sequence comprising SEQ ID NO:6, SEQ ID NO:7 or SEQ ID NO:8; b) a nucleic acid sequence comprising at least 65% sequence identity to SEQ ID NO:6, SEQ ID NO:7 or SEQ ID NO:8; and c) a fragment of the nucleic acid sequence of SEQ ID NO:6, SEQ ID NO:7 or SEQ ID NO:8. In particular embodiments, the polynucleotide molecule may comprise at least about 65%, at least about 85%, at least about 90%, at least about 95% identity, or at least about 98% identity to the nucleic acid sequence of SEQ ID NO:6, SEQ ID NO:7 or SEQ ID NO:8. The polynucleotide molecule may comprise the sequence of SEQ ID NO:6, SEQ ID NO:7 or SEQ ID NO:8. The polynucleotide molecule may also be defined as comprising a fragment of the nucleic acid sequence of SEQ ID NO:6, SEQ ID NO:7 or SEQ ID NO:8. In further embodiments, the polynucleotide molecule may be operably linked to a heterologous transcribable polynucleotide molecule, including, for example, a heterologous transcribable polynucleotide molecule that encodes a selectable marker. Examples of such selectable markers include those that confer resistance to a selective agent selected from the group consisting of: kanamycin, spectinomycin, streptomycin, hygromycin, gentamycin, glyphosate, dicamba, and glufosinate. In one embodiment, the selectable marker is aadA.

In yet another aspect, the invention provides a transgenic cell transformed with a polynucleotide described herein. In specific embodiments, the cell is a prokaryotic cell, and may be a bacterial cell, including a member of the *Rhizobiales*. The *Rhizobiales* may be selected from the group consisting of: *Rhizobium* spp., *Sinorhizobium* spp., *Mesorhizobium* spp., *Phyllobacterium* spp., *Ochrobactrum* spp., and *Bradyrhizobium* spp. In one embodiment, the bacterial cell is an *E. coli* cell.

In still yet another aspect, the invention provides a transgenic organelle comprising the polynucleotide molecule of claim 1.

Still further provided by the invention is a recombinant *Agrobacterium* cell wherein the function of the native virE operon promoter of the cell has been replaced with a heterologous constitutive promoter. The cell may be an *Agrobacterium tumefaciens* cell. In specific embodiments, the heterologous promoter may comprise a promoter sequence provided herein.

Another aspect of the invention provides a method for enhancing expression of a transgene in a prokaryotic cell comprising: (a) transforming the cell with a transgene operably linked to a 16S rDNA promoter operably linked to a ribosomal binding site; (b) growing the cell; and (c) testing the cell for enhanced expression of the transgene. In one embodiment, the transgene confers a commercially important trait. In another embodiment, the method further comprises the step of: (d) harvesting a product of the enhanced expression of the transgene. In yet another embodiment of the method, the product of the enhanced transgene expression is a protein or a compound.

BRIEF DESCRIPTION OF THE DRAWINGS

FIG. 1. Alignment of *Agrobacterium tumefaciens* C58 16S rDNA promoter sequences (SEQ ID NOs: 1-4) and the consensus sequence (SEQ ID NO:5). Arrow under G indicates the isolated promoter's starting base pair. Arrow under A indicates potential 16S rRNA initiation site; a HindIII site is underlined.

FIG. 2. The long P-rrn promoter (SEQ ID NO:1).

FIG. 3. The short P-rrn promoter (SEQ ID NO:1).

FIG. 4. The long P-rrn promoter with filled-in HindIII site (underlined). (SEQ ID NO:1).

DESCRIPTION OF SEQUENCE LISTING

Figure 5:
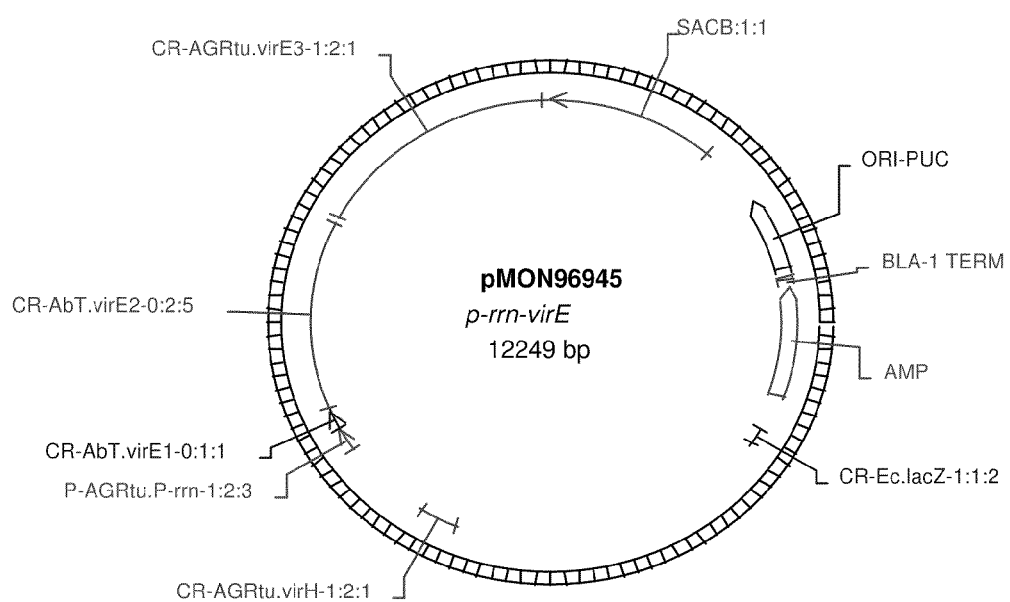
FIG. 5. Diagrammatic representation of plasmid pMON96945.
Figure 6:
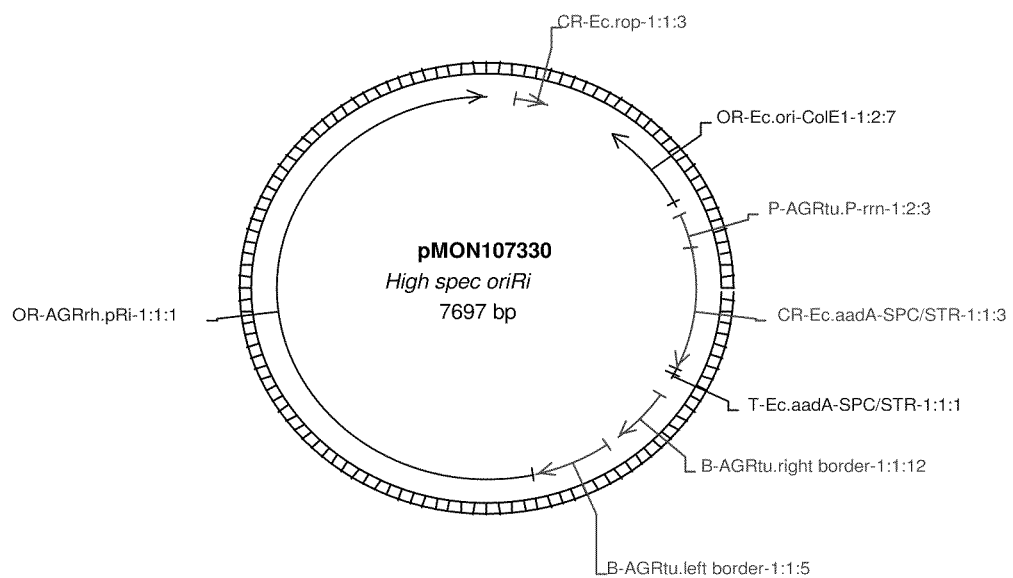
FIG. 6. Diagrammatic representation of plasmid pMON107330. pMON107330 is a 1 T-DNA low copy oriRi vector carrying the long P-rrn with aadA which confers on *Agrobacterium* the ability to tolerate spectinomycin concentration over 300 mg/l, causing the culture to grow faster than a culture containing cells with a multiple copy oriV vector.
Figure 7:
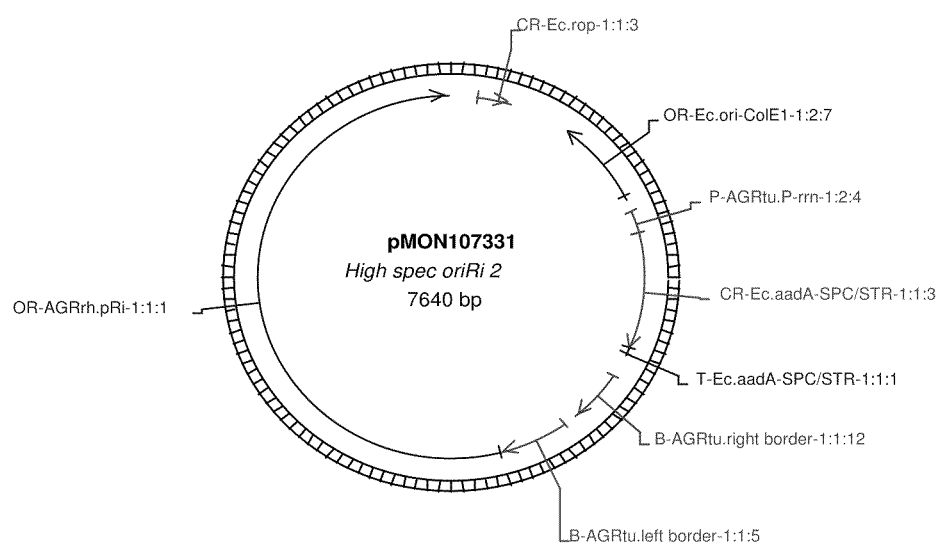
FIG. 7. Diagrammatic representation of plasmid pMON107331. pMON107331 is a 1 T-DNA low copy oriRi vector carrying the short P-rrn with aadA which confers the same spectinomycin resistance as the long P-rrn with aadA in *E. coli* but in *Agrobacterium* the resistance substantially is reduced.
Figure 8:
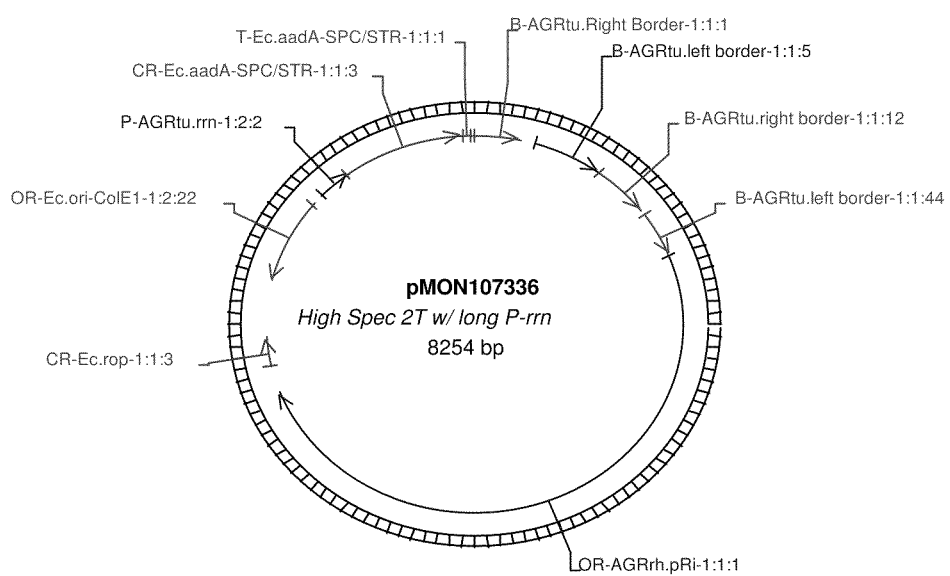
FIG. 8. Diagrammatic representation of plasmid pMON107336. pMON107336 is a 2 T-DNA low copy oriRi vector carrying the long P-rrn with aadA.
Figure 9:
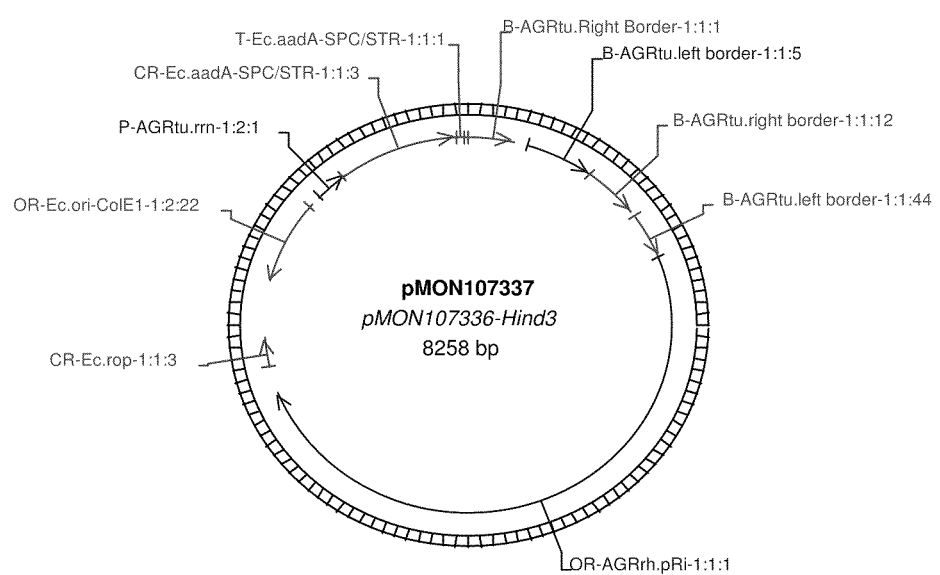
FIG. 9. Diagrammatic representation of plasmid pMON107337. pMON107337 is a 2 T-DNA low copy oriRi vector carrying the HindIII minus P-rrn with aadA.

A summary of sequences referred to herein is provided below.

| SEQ ID NO | Organism/source | Details | From | Identified from GenBank Accession No. |
|---|---|---|---|---|
| 1 | *Agrobacterium tumefaciens* C58 | Identified enhancer and promoter element | gDNA | AE009201, AE008688 |
| 2 | *Agrobacterium tumefaciens* C58 | Identified enhancer and promoter element | gDNA | AE008980, AE008688 |
| 3 | *Agrobacterium tumefaciens* C58 | Identified enhancer and promoter element | gDNA | AE009324, AE008689 |
| 4 | *Agrobacterium tumefaciens* C58 | Identified enhancer and promoter element | gDNA | AE009348, AE008689 |
| 5 | *Agrobacterium tumefaciens* C58 | Consensus of SEQ ID NOs: 1-4 | N/A | N/A |
| 6 | Synthetic (En + Pro + RBS + ATG) | Synthetic promoter sequence | N/A | N/A |
| 7 | Synthetic (Pro + RBS + ATG) | Synthetic promoter sequence | N/A | N/A |
| 8 | Synthetic (En + Pro + RBS + ATG − HindIII site) | Synthetic promoter sequence | N/A | N/A |
| 9-21 | Primers for amplification, cloning, and/or analysis of | Synthetic | N/A | N/A |

-continued

| SEQ ID NO | Organism/source | Details | From | Identified from GenBank Accession No. |
|---|---|---|---|---|
| | P-rrn sequences and constructs | | | |
| 22-25 | Rhizobium leguminosarum bv. viciae 3841 | Identified enhancer and promoter element and consensus sequence | gDNA | NC_008380 |
| 26-29 | Rhizobium etli CFN 42 | Identified enhancer and promoter element and consensus sequence | gDNA | NC_007761 |
| 30-33 | Sinorhizobium medicae WSM419 | Identified enhancer and promoter element and consensus sequence | gDNA | CP000738 |
| 34-37 | Sinorhizobium meliloti 1021 | Identified enhancer and promoter element and consensus sequence | gDNA | NC_003047 |

DETAILED DESCRIPTION OF THE INVENTION

A strong prokaryotic promoter (P-rrn) from the 16S rDNA gene of *A. tumefaciens* C58 strain which specifies a high level of gene expression in both *E. coli* and *Agrobacterium* has now been identified and characterized. The isolated promoter is useful for over-expressing genes, for example, in *E. coli* and *Agrobacterium*, conferring a high level of gene expression in low copy vectors, reducing cloning time and quality control time due to faster growth, and reducing *Agrobacterium* growth variations due to low copy vectors.

The P-rrn promoter from *Agrobacterium* C58 when fused to the aadA gene confers in both *E. coli* and *Agrobacterium* high level resistance to spectinomycin. In *E. coli*, P-rrn-aadA vectors allow harvesting of cells in 5-6 hours, while use of a native aadA promoter requires about 8 hours. The enhanced growth of *E. coli* containing a vector comprising the P-rrn promoter can speed up the cloning process. In *Agrobacterium*, a P-rrn-aadA construct confers resistance to application of spectinomycin at over 300 mg/L. In the range of spectinomycin level of 75-300 mg/l, *Agrobacterium* cultures with the oriRi vectors with P-rrn-aadA showed 0.1-0.2 higher ODs at OD600 after overnight culture compared to multicopy oriV vectors.

The invention thus provides polynucleotide molecules having gene regulatory activity. In one embodiment, examples of such sequences are provided by the chimeric polynucleotides of SEQ ID NOs: 6-8. Such polynucleotide molecules are capable of directing the expression of an operably linked transcribable polynucleotide molecule in bacterial cells. The present invention also provides methods of modifying, producing, and using the same. The invention further provides compositions, transformed host cells, and methods for preparing and using the same.

The invention describes the identification and isolation of a 16S rRNA promoter (P-rrn) from a member of the Rhizobiales, and more specifically *Agrobacterium tumefaciens* and describes the features of this promoter. The promoter has been shown to exhibit a variety of properties. One of the properties described herein is the identification of a segment of the P-rrn promoter that enhances growth of *E. coli* and *Agrobacterium tumefaciens* cells under selection pressure.

The invention also provides, in specific embodiments, organelles transformed with a polynucleotide sequence described herein. Methods for the creation of transgenic organelles, including plant plastids, are well known in the art and described in, for example U.S. Pat. Nos. 6,492,578 and 6,218,145.

Polynucleotide Molecules

The following definitions and methods are provided to better define the present invention and to guide those of ordinary skill in the art in the practice of the present invention. Unless otherwise noted, terms are to be understood according to conventional usage by those of ordinary skill in the relevant art.

The phrases "coding sequence," "structural sequence," and "transcribable polynucleotide sequence" refer to a physical structure comprising an orderly and contiguous linear arrangement of nucleic acids. The nucleic acids are arranged in a series of nucleic acid triplets that each form a codon when viewed within a particular reading frame along the length of the contiguous linear arrangement of nucleic acids. Each codon encodes for a specific amino acid. Thus the coding sequence, structural sequence, and transcribable polynucleotide sequence encode a series of amino acids forming a protein, polypeptide, or peptide sequence. The "coding sequence," "structural sequence," and "transcribable polynucleotide sequence" encode a series of amino acids forming a protein, polypeptide, or peptide sequence. The coding sequence, structural sequence, and transcribable polynucleotide sequence may be contained, without limitation, within a larger nucleic acid molecule, vector, etc. In addition, the orderly arrangement of nucleic acids in these sequences may be depicted, without limitation, in the form of a sequence listing, figure, table, electronic medium, and the like.

As used herein, the term "polynucleotide molecule or polynucleic acid molecule" refers to the single- or double-stranded DNA or RNA molecule of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for nucleotide bases as used herein can be found in Part 1 of Title 37 of the United States Code of Federal Regulations, in particular at section 1.822 is used herein.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are polynucleotide molecules having gene regulatory activity which play an integral part in the overall expression of genes in living cells. Isolated regulatory elements that function in bacteria are therefore useful for modifying their phenotypes through the methods of genetic engineering. By "regulatory element" is intended a series of nucleotides that determines if, when, and at what level a particular gene is expressed. The regulatory DNA sequences specifically interact with regulatory proteins or other proteins.

By "promoter activity" it is meant that a nucleic acid is capable of serving as a promoter element and thus directing the transcription of an operably linked transcribable polynucleotide molecule.

As used herein, the term "operably linked or linked" refers to a first polynucleotide molecule joined to a second polynucleotide wherein the polynucleotide molecules are so arranged that the first polynucleotide molecule affects the function of the second polynucleotide molecule. The two polynucleotide molecules may be part of a single contiguous polynucleotide molecule and may be adjacent. In some embodiments a promoter enhancer is operably linked to a promoter and/or a promoter is operably linked to a polynucleotide of interest so that the promoter modulates transcription of the linked polynucleotide molecule of interest in a cell.

As used herein, the term "gene regulatory activity" refers to a polynucleotide molecule capable of affecting transcription or translation of an operably linked polynucleotide molecule. An isolated polynucleotide molecule having gene regulatory activity may provide temporal expression or modulate levels and rates of expression of the operably linked transcribable polynucleotide molecule. An isolated prokaryotic polynucleotide molecule having gene regulatory activity may comprise a promoter, ribosomal binding site, additional transcription factor binding site(s), or 3' transcriptional termination region.

As used herein, the term "gene expression" or "expression" refers to the transcription of a DNA molecule into a transcribed RNA molecule. Gene expression may be described as related to temporal, quantitative or qualitative indications. The transcribed RNA molecule may be translated to produce a protein molecule or may provide an antisense or other regulatory RNA molecule, such as a dsRNA, a tRNA, a rRNA, and the like.

As used herein, an "expression pattern" is any pattern of differential gene expression. In certain embodiments, an expression pattern may be characterized as one or more of temporal, stress, environmental, physiological, pathological, cell cycle, and/or chemically responsive expression patterns.

As used herein, the term "transcribable polynucleotide molecule" refers to any polynucleotide molecule capable of being transcribed into a RNA molecule, including but not limited to protein coding sequences and sequences useful for gene suppression.

A "transgene" comprises a DNA molecule heterologous to a host cell.

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one molecule is complementary to its base pairing partner nucleotide in another molecule. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., (Molecular Cloning: A Laboratory Manual $2^{nd}$ Ed., Cold Spring Harbor Laboratory Press, 1989) herein referred to as Sambrook et al., 1989, and by Haymes et al., (Nucleic Acid Hybridization, A Practical Approach, IRL Press, Washington, D.C., 1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) Ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with an incubation at 55° C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

A chimeric promoter polynucleic acid molecule of the present invention preferably comprises a P-rrn promoter polynucleic acid sequence that hybridizes, under low or high stringency conditions, with any of SEQ ID NOs: 6-8, any complements thereof, or any fragments thereof, or any cis elements thereof. In a particular embodiment, the invention provides a segment of the P-rrn promoter that allows for growth of E. coli or Agrobacterium cells in the presence of a selective agent, wherein a polynucleotide sequence encoding a gene product that specifies tolerance or resistance to the selective agent is operably linked to the P-rrn promoter.

In another embodiment, the invention provides a segment of a P-rrn promoter that drives the expression of a transgene, for instance in a prokaryote such as E. coli, that results in production of a protein of commercial importance or whose product results in production of a commercially important compound. In other embodiments, the promoters of the present invention are used to replace native promoters of certain genes such as those of one or more of the virB operon, virC operon, virD operon, and/or virE operon in a host organism such as *Agrobacterium* to enhance expression of these genes. Enhanced expression of the virB operon, virC operon, and virD operon is known to result in enhanced cell transformation frequency by *Agrobacterium*, and enhanced expression of the virE operon is known to provide for more efficient transfer of large T-DNA segments to cells.

Analysis of Sequence Similarity Using Identity Scoring

As used herein, the term "sequence identity" refers to the extent to which two optimally aligned polynucleotide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, for instance provided herein as any of SEQ ID NOs:1-8 and SEQ ID NOs:22-37, has at least 65 percent identity or higher, has at least 70 percent identity or higher, has at least 75 percent identity or higher, has at least 80 percent identity or higher, about 85 percent identity or higher, about 90 percent identity or higher, about 95 percent identity or higher, or at least 96 percent identity, 97 percent identity, 98 percent identity, or 99 percent identity to the reference sequence, and has gene regulatory activity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as at least about 95%, 98% or 99% sequence identity with a polynucleotide sequence described herein. Polynucleotide molecules and variants thereof that are capable of regulating transcription of operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins Polynucleotide Molecules, Motifs, Fragments, Chimeric Molecules, Enhancers As used herein, the term "enhancer domain" refers to a cis-acting transcriptional regulatory element (cis-element), which confers an aspect of the overall modulation of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation. Any of the polynucleotide molecules of the present invention may comprise an enhancer.

Chimeric promoter molecules of the present invention combine a 16S rDNA enhancer molecule, a P-rrn promoter molecule, and virE operon ribosomal binding site (RBS) that confers or modulates gene expression from the promoter. Chimeric promoter without the enhancer molecule was found to be sufficient for enhanced growth of *E. coli* cells under selection pressure. However, the enhancer molecule is required for enhanced growth of *Agrobacterium* under selection pressure. Other suitable promoter enhancer molecules and RBS molecule could be used in the practice of the present invention.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in bacteria and are considered to be within the scope of this invention. Thus, the design, construction, and use of chimeric regulatory elements are one aspect of this invention.

As used herein, the term "fragment," "fragment thereof," or "segment" refers in specific embodiments to fragments of a promoter that are provided, comprising at least about 50, 95, 150, 250, 500, or about 750 contiguous nucleotides of a polynucleotide molecule having promoter activity disclosed herein. These fragments may exhibit promoter activity, and may be useful alone or in combination with other promoters or promoter fragments, such as in constructing chimeric promoters.

Promoters

Among the gene expression regulatory elements, the promoter plays a central role. Along the promoter molecule, the transcription machinery is assembled and transcription is initiated. This early step is often rate-limiting relative to subsequent stages of protein production. Transcription initiation at the promoter may be regulated in several ways. For example, a promoter may be induced by the presence of a particular compound or external stimuli, express a gene during a specific stage of development, or constitutively express a gene. Thus, transcription of a transgene may be regulated by operably linking the coding sequence to promoters with different regulatory characteristics. Accordingly, a regulatory element such as a promoter, plays a pivotal role in enhancing the value of a transgenic organism.

As used herein, the term "promoter" refers to a polynucleotide molecule that is involved in recognition and binding of RNA polymerase and other proteins such as associated sigma factor and an activator protein to initiate transcription of an operably linked gene. A promoter may be isolated from the 5' untranslated region (5' UTR) of a genomic copy of a gene.

Alternately, a promoter molecule may be artificially and synthetically produced or comprise modified DNA sequence. A promoter can be used as a regulatory element for modulating expression of an operably linked transcribable polynucleotide molecule. Promoters may themselves contain sub-elements such as cis-elements or enhancer domains that effect the transcription of operably linked genes.

In prokaryotes, the promoter consists of two short sequences at −10 and −35 positions upstream from the transcription start site. Sigma factors not only help in enhancing RNAP binding to the promoter but helps RNAP target which genes to transcribe. The sequence at −10 is called the Pribnow box, or the −10 element, and usually consists of the six nucleotides TATAAT. The Pribnow box is absolutely essential to start transcription in prokaryotes. The other sequence at −35 (the −35 element) usually consists of the six nucleotides TTGACA. Its presence allows a very high transcription rate. Both of the above consensus sequences, while conserved on average, are not found intact in most promoters. On average only 3 of the 6 base pairs in each consensus sequence is found in any given promoter. It should be noted that the above promoter sequences are only recognized by the sigma-70 protein that interacts with the prokaryotic RNA polymerase. Complexes of prokaryotic RNA polymerase with other sigma factors recognize totally different core promoter sequences.

Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation. Cis elements occur within the 5' UTR associated with a particular coding sequence, and are often found within promoters and promoter modulating sequences (inducible elements). Cis elements can be identified using known cis elements as a target sequence or target motif using the BLAST programs. Examples of cis-acting elements in the 5'UTR associated with a polynucleotide coding sequence include, but are not limited to, promoters and enhancers.

In prokaryotes, the mRNA translation starts with UTG, GTG or in rare case UUG, which is usually preceded by sequences characteristic of a ribosomal binding site (RBS; Shine and Dalgarno, *PNAS* 71:1342-1346, 1974). The RBS is AG rich and usually is found 6-12 bp before initiation codon. The RBS is believed to be necessary for efficient mRNA translation in bacteria. The *Agrobacterium* and other *Rhizobiaceae* 16S P-rrn promoters appear to not contain a consensus RBS to facilitate efficient translation. An additional RBS, for instance from another operon, may be fused to the 3' end of the P-rrn for efficient translation.

In specific embodiments, promoter molecules are provided that exhibit 65% or greater identity, 70% or greater identity, 75% or greater identity, 80% or greater identity, 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a polynucleic acid segment selected from the group consisting of SEQ ID NO:6, SEQ ID NO:7 and SEQ ID NO:8.

At least two types of information are useful in predicting promoter regions within a genomic DNA sequence. First, promoters may be identified on the basis of their sequence "content," such as transcription factor binding sites and various known promoter motifs. (Stormo, *Genome Research* 10: 394-397, 2000). Such signals may be identified by computer programs that identify sites associated with promoters, such as TATA boxes and transcription factor (TF) binding sites. Second, promoters may be identified on the basis of their "location," i.e. their proximity to a known or suspected coding sequence (Stormo). Prokaryotic promoters are typically found within a region of DNA extending approximately 1-500 basepairs in the 5' direction from the transcriptional or translational start codon of a coding sequence. Thus, promoter regions may be identified by locating the translational start codon of a coding sequence or the transcriptional start site, and moving beyond the start codon in the 5' direction to locate the promoter region.

Promoter sequence may be analyzed for the presence of common promoter sequence characteristics, such as a TATA-box and other known transcription factor binding site motifs. These motifs are not always found in every known promoter, nor are they necessary for every promoter to function, but when present, do indicate that a segment of DNA is a promoter sequence.

The activity or strength of a promoter may be measured in terms of the amount of mRNA tRNA, dsRNA, miRNA, rRNA, or protein is specifically accumulated during a particular period of time in the growth of a cell containing the transgene. An enhanced level of mRNA production may be required to produce a protein of commercial importance, or a protein for catalyzing a reaction to produce a compound of commercial importance. Coding sequences for the commercially important proteins can be identified by those skilled in the art and can be used with the promoters of the invention to effect production of mRNA and protein levels. The activity or strength of a promoter can also be measured in terms of enhanced cell growth when a cell is grown under selection pressure after it has been transformed with, for instance, a gene that allows for detoxification of a compound under the control of the promoter.

Regulatory Element Isolation and Modification

Any number of methods well known to those skilled in the art can be used to isolate a polynucleotide molecule, or fragment thereof, disclosed in the present invention. For example, is PCR (polymerase chain reaction) technology can be used to amplify flanking regions from a particular starting nucleotide sequence. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from *Agrobacterium* genomic DNA by designing oligonucleotide primers based on available sequence information and using PCR techniques to extract a particular segment of DNA.

As used herein, the term "isolated polynucleotide molecule" refers to a polynucleotide molecule at least partially separated from other molecules normally associated with it in its native state. In one embodiment, the term "isolated" is also used herein in reference to a polynucleotide molecule that is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed. Use of these probes may greatly facilitate the identification of transgenic organisms which contain the presently disclosed nucleic acid molecules. The probes may also be used to screen genomic libraries for additional nucleic acid sequences related or sharing homology to the presently disclosed promoters. The short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3, STSPipeline, or GeneUp (Pesole, et al., *BioTechniques* 25:112-123, 1998), for example, can be used to identify potential PCR primers.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g. related nucleic acid sequences from other species).

The primer or probe is generally complementary to a portion of a nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long. The primer or probe may be prepared by direct chemical synthesis, by PCR (for example, U.S. Pat. Nos. 4,683,195, and 4,683,202), or by excising the nucleic acid specific fragment from a larger nucleic acid molecule.

Regulatory Elements in a DNA Construct

Various regulatory sequences may be included in a recombinant DNA construct. Any such regulatory sequences may be provided in a recombinant vector with other regulatory sequences. Such combinations can be designed or modified to produce desirable regulatory features. Constructs of the present invention would typically comprise one or more gene expression regulatory elements operably linked to a transcribable polynucleotide molecule operably linked to an optional 3' transcription termination polynucleotide molecule. As used herein, the term "heterologous ribosomal binding site" refers to a heterologous nucleotide sequence on mRNA that is bound by the ribosome when initiating protein translation.

As used herein, the term "leader" refers to a polynucleotide molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements.

DNA Constructs

The DNA constructs of the present invention are generally double Ti plasmid border DNA constructs that have the right border (RB or AGRtu.RB) and left border (LB or AGRtu.LB) regions of the Ti plasmid isolated from *Agrobacterium* comprising a T-DNA, that along with transfer molecules provided by the *Agrobacterium* cells, permit the integration of the T-DNA into the genome of a plant cell (see for example U.S. Pat. No. 6,603,061, herein incorporated by reference in its entirety). The constructs may also contain the plasmid backbone DNA segments that provide replication function and antibiotic selection in bacterial cells, for example, an *Escherichia coli* origin of replication such as ori322, or ColE1, an *Agrobacterium* origin of replication, such as oriV or oriRi, and a coding region for a selectable marker such as aadA that encodes for Tn7 aminoglycoside adenyltransferase (aadA) conferring resistance to spectinomycin or streptomycin, or a gentamicin (Gm, Gent) selectable marker gene. For bacterially mediated plant transformation, the host bacterial strain is often *Agrobacterium tumefaciens* ABI, C58, EHA101, EHA105, AGLO, or AGLI, or LBA4404, however, other strains known to those skilled in the art of plant transformation can function in the present invention.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see for example, *Molecular Cloning: A Laboratory Manual, 3rd edition* Volumes 1, 2, and 3 (2000) J. F. Sambrook, D. W. Russell, and N. Irwin, Cold Spring Harbor Laboratory Press). Methods for making recombinant vectors particularly suited to plant transformation include, without limitation, those described in U.S. Pat. Nos. 4,971,908, 4,940, 835, 4,769,061 and 4,757,011, all of which are herein incorporated by reference in their entirety. These types of vectors have also been reviewed (Rodriguez, et al. *Vectors: A Survey of Molecular Cloning Vectors and Their Uses*, Butterworths, Boston, 1988; Glick et al., *Methods in Plant Molecular Biology and Biotechnology*, CRC Press, Boca Raton, Fla., 1993). Typical vectors useful for expression of nucleic acids in higher plants are well known in the art and include vectors derived from the tumor-inducing (Ti) plasmid of *Agrobacterium tumefaciens* (Rogers, et al., *Meth. In Enzymol,* 153: 253-277, 1987). Other recombinant vectors useful for plant transformation, including the pCaMVCN transfer control vector, have also been described (Fromm et al., *Proc. Natl. Acad. Sci. USA,* 82: 5824-5828, 1985).

Transcribable Polynucleotide Molecules

A promoter or chimeric promoter molecule of the present invention may be operably linked to a transcribable polynucleotide sequence that is heterologous with respect to the promoter molecule. The term "heterologous" refers to the relationship between two or more polynucleic acid or protein sequences that are derived from different sources. For example, a promoter or ribosome binding site is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

The transcribable polynucleotide molecule may generally be any polynucleic acid sequence for which an increased level or differential cell expression of a transcript is desired. Alternatively, the regulatory element and transcribable polynucleotide sequence may be designed to down-regulate a specific polynucleic acid sequence. This is typically accomplished by linking the promoter to a transcribable polynucleotide molecule that is oriented in the antisense direction. One of ordinary skill in the art is familiar with such antisense technology. Briefly, as the antisense polynucleic acid molecule is transcribed, it hybridizes to and sequesters a complimentary polynucleic acid molecule inside the cell. This duplex RNA molecule cannot be translated into a protein by the cell's translational machinery and is degraded in the cell. Any polynucleic acid molecule may be negatively regulated in this manner.

A regulatory element of the present invention may also be operably linked to a modified transcribable polynucleotide molecule that is heterologous with respect to the promoter. The transcribable polynucleotide molecule may be modified to provide various desirable features. For example, a transcribable polynucleotide molecule may be modified to increase the content of essential amino acids, to enhance translation of the amino acid sequence, to enhance transport of a translated product to a compartment inside or outside of a cell, or to improve protein stability, among other effects.

Due to the degeneracy of the genetic code, different nucleotide codons may be used to code for a particular amino acid. A host cell often displays a preferred pattern of codon usage. Transcribable polynucleotide molecules are preferably constructed to utilize the codon usage pattern of the particular host cell. This generally enhances the expression of the transcribable polynucleotide molecule in a transformed host cell. Any of the polynucleic acids may be modified to reflect the preferred codon usage of a host cell or organism in which they are contained. Modification of a transcribable polynucleotide molecule for optimal codon usage is described, for example, in U.S. Pat. No. 5,689,052.

Additional variations in the transcribable polynucleotide molecules may encode proteins having equivalent or superior characteristics when compared to the proteins from which they are engineered. Mutations may include, but are not limited to, deletions, insertions, truncations, substitutions, fusions, shuffling of motif sequences, and the like. Mutations to a transcribable polynucleotide molecule may be introduced in either a specific or random manner, both of which are well known to those of skill in the art of molecular biology.

Thus, one embodiment of the invention is a chimeric promoter molecule of the present invention, such as provided in SEQ ID NOs: 6-8 or variant thereof, operably linked to a transcribable polynucleotide molecule so as to modulate transcription of the transcribable polynucleotide molecule at a desired level or in developmental pattern upon introduction of the construct into a cell. In one embodiment, the transcribable polynucleotide molecule comprises a protein-coding region of a gene, and the chimeric promoter molecule affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Genes of Commercial Interest

As used herein, the term "gene of commercial interest" refers to a transcribable polynucleotide molecule that includes but is not limited to a DNA coding sequence or other element intended for expression in the cell, and when expressed in a particular cell or cell type provides a desirable characteristic associated with morphology, physiology, growth and development, exhibiting an effect upon the yield of the cell or cell product, nutritional enhancement, or environmental or chemical tolerance. Suitable transcribable polynucleotide molecules include but are not limited to those encoding traits for desirable biosynthetic, chemical, insecticidal, industrial, nutritional, or pharmaceutical properties. For examples, polynucleotide for producing rBGH, antibodies, enzymes for biotechnology applications, and enzymes such as cellulose, glucanase and other hydrolysis enzymes for feed industry. Suitable transcribable polynucleotide molecules include but are not limited to those encoding any other agent such as a dsRNA molecule targeting a particular gene for suppression either within the cell in order to cause an effect upon the plant physiology or metabolism or to be provided as a pesticidal agent in the diet of a pest that feeds on the cell.

In one embodiment of the invention, a polynucleotide molecule as shown in SEQ ID NOs: 6-8 or variants thereof, is incorporated into a construct such that the polynucleotide molecule of the present invention is operably linked to a transcribable polynucleotide molecule that is a gene of commercial interest.

The expression of a gene of commercial interest is desirable in order to confer a commercially important trait. A gene of commercial interest (a transcribable polynucleotide molecule) that provides a beneficial commercial trait to a prokaryotic cell may include, for example, but are not limited to, genes that lead to production of pigments (e.g., melanin by tyrosinase), antibiotics, biofuels (e.g., butanol and pentanol), biodegradable plastics (e.g., PHA; polyhydroxyalkanoate), textiles (e.g., spider silk), to break down of atmospheric pollutants, production of glucaric acid (e.g., used in synthesis of nylons, and water treatment), tyrosine (a building block for drugs and food additives), biopolymers, hyaluronic acid (a natural joint lubricant that can be used to treat arthritis), or isoprenoids (for the biosynthesis of many important pharmaceutical compounds). Other genetic elements may also be utilized, for instance selected from among ones conferring starch production (U.S. Pat. Nos. 6,538,181; 6,538,179; 6,538,178; 5,750,876; 6,476,295), modified oil production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), biopolymers (U.S. Pat. Nos. RE37,543; 6,228,623; 5,958,745 and U.S. Patent Publication No. US20030028917), pharmaceutical peptides and secretable peptides (U.S. Pat. Nos. 6,812,379; 6,774,283; 6,140,075; 6,080,560), improved processing traits (U.S. Pat. No. 6,476,295), industrial enzyme production (U.S. Pat. No. 5,543,576), and biofuel production (U.S. Pat. No. 5,998,700).

Alternatively, a transcribable polynucleotide molecule can effect the above mentioned cell characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a commercially important phenotype or morphology change of interest may be useful for the practice of the present invention.

Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in cells is disclosed in U.S. Pat. No. 5,107,065 and U.S. Pat. No. 5,759,829; posttranscriptional gene suppression using a construct with a sense-oriented transcribable polynucleotide molecule to regulate gene expression is disclosed in U.S. Pat. No. 5,283,184 and U.S. Pat. No. 5,231,020. Expression of a transcribable polynucleotide in a cell can also be used to suppress pests feeding on the cell, for example, compositions isolated from coleopteran pests (U.S. Patent Application Publication 20070124836, herein incorporated by reference in its entirety) and compositions isolated from nematode pests (U.S. Patent Application Publication 20070250947, herein incorporated by reference in its entirety).

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods. The type of polynucleotide molecule can include but is not limited to a polynucleotide molecule that is already present in the cell, a polynucleotide molecule from another cell, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670, which is incorporated herein by reference), green fluorescent protein and variants thereof (GFP described in U.S. Pat. No. 5,491,084 and U.S. Pat. No. 6,146,826, RFP and the like, all of which are incorporated herein by reference), proteins that confer antibiotic resistance, or proteins that confer herbicide tolerance.

Useful antibiotic resistance markers, including those encoding proteins conferring resistance to kanamycin (nptII), hygromycin B (aph IV), streptomycin or spectinomycin (aad, spec/strep), and gentamycin (aac3 and aacC4) are known in the art, among others.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

In specific embodiments, a selectable marker use may be GUS, green fluorescent protein (GFP), neomycin phosphotransferase II (nptII), luciferase (LUX), an antibiotic resistance coding sequence (aadA), or an herbicide (e.g., glyphosate, dicamba, glufosinate, or 2,4-D) resistance coding sequence. In certain embodiments, the selectable marker is a kanamycin, streptomycin and/or spectinomycin resistance marker. Examples of coding sequences providing tolerance to antibiotics and herbicides can be found, for instance, in US Patent Application Publications 20080305952 and 20080280361, which are incorporated herein by reference.

Cell Transformation

The invention is also directed to a method of producing transformed cells which comprise, in a 5' to 3' orientation, a chimeric promoter operably linked to a heterologous transcribable polynucleotide molecule. Other molecules may also be introduced into the cell, including 3' transcriptional terminators, 3' polyadenylation signals, other translated or untranslated sequences, transit or targeting sequences, selectable markers, enhancers, and operators.

The term "transformation" refers to the introduction of nucleic acid into a recipient host. The term "host" refers to prokaryotic cells, especially bacterial cells. As used herein, the term "transformed" refers to a cell or organism into which has been introduced a foreign polynucleotide molecule, such as a construct. The introduced polynucleotide molecule may be integrated into the genomic DNA of the recipient cell or organism such that the introduced polynucleotide molecule is inherited by subsequent progeny or may stay in cytoplasm as a self replicating unit. A "transgenic" or "transformed" cell or organism also includes progeny of the cell or organism. The term "transgenic" refers to a cell or other organism containing one or more heterologous polynucleic acid molecules.

There are many methods for introducing heterologous polynucleic acid molecules into cells. The method generally comprises the steps of selecting a suitable host cell, transforming the host cell with a recombinant vector, and obtaining the transformed host cell. Suitable methods for introducing heterologous polynucleic acid molecules into prokaryotes include Freeze-thaw (Heat shock), triparental mating, and electroporation, among others. These methods are known to those skilled in the art of prokaryotic transformation.

Any of the above described methods may be utilized to transform a host cell with one or more gene regulatory elements of the present invention and one or more transcribable polynucleotide molecules. The host cell may be any prokaryotic cell, including both Gram negative and Gram positive bacteria. Suitable bacteria include, without limitation, *Escherichia* sp., *Salmonella* sp., *Klebsiella*, *Proteus*, *Yersinia*, *Azotobacter* sp., *Pseudomonas* sp., *Xanthomonas* sp., *Agrobacterium* sp., *Alcaligenes* spp., *Bordetella* sp., *Haemophilus influenzae*, *Methylophilus methylotrophus*, *Rhizobium* sp., *Thiobacillus* sp., *Streptomyces* sp., and *Clavibacter* sp. Preferably, the host cell is selected from among *E. coli*, *Agrobacterium* sp., *Rhizobium* sp., *Sinorhizobium* sp., *Mesorhizobium* sp., *Phyllobacterium* sp. *Ochrobactrum* sp. and *Bradyrhizobium* sp.

The transformed cells are analyzed for the presence of the genes of interest and the expression level and/or profile conferred by the regulatory elements of the present invention. Those of skill in the art are aware of the numerous methods available for the analysis of transformed cells. For example, methods for cell analysis include, but are not limited to Southern blots or northern blots, PCR-based approaches, biochemical analyses, phenotypic screening methods, plate assays, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used for transgene expression. Primer sets (pairs of DNA molecules that specifically hybridize to a target polynucleotide molecule) are developed to identify specific transcribed transgene sequences. For example, the expression of transcript of the present invention can be identified and measured in the sample using DNA primer molecules or OD at particular absorbance. Primer molecules can be selected by those skilled in the art from DNA sequences disclosed herein or other DNA sequences comprising any transgene transcript from which the expression is driving by a chimeric promoter molecule of the present invention that measures the presence or expression levels of the transgene transcripts.

Having now generally described the invention, the same will be more readily understood through reference to the following examples which are provided by way of illustration, and are not intended to be limiting of the present invention, unless specified. Each periodical, patent, and other document or reference cited herein is herein incorporated by reference in its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Isolation of a 16S rDNA Promoter and Construction of Chimeric P-rrn Promoter Sequences Four copies of the 16S rDNA are present in *A. tumefaciens* strain C58. Putative promoter length was determined by aligning four copies of the gene retrieved from Genbank (see FIG. 1) and a consensus sequence was obtained which was PCR-amplified from the genomic DNA using standard methods. As the native 16S rDNA promoter does not contain a Ribosomal Binding Site (RBS), the promoter was first cloned with a virE operon to operably link the RBS of the virE operon with the 3' end of the promoter.

Xd775:
(SEQ ID NO: 9)
5' GGactagtGGTCTGTTTTTTGACAATTGAATATGAGAAG 3'
(P-rrn 5' forward)

Xd776:
(SEQ ID NO: 10)
5' cgcatttagcttgatgatcaccatGGCTTTGTTTCTCCTTCAATCAT
TGACTATTGTCACGTTATTCTG 3'

Xd777:
(SEQ ID NO: 11)
5' CgggcccACACTTGAATCGGTAATTTCATTCTAAAGTG 3'
(virE3 reverse)

Primers Xd775 and Xd776 were used to amplify P-rrn from the C58 genomic DNA using the pfu polymerase. After 10 PCR cycles, the amplified DNA was mixed with pTiC58 DNA comprising virE operon and Xd777 and amplified for additional 5 cycles with 4.5 min elongation time. One µl of the product was further amplified with the primers Xd775 and Xd777 to amplify DNA comprising the P-rrn and virE1 to virE3 (4.3 kb) coding region. The amplified fragment was gel isolated and cloned into pCR® Blunt II TOPO® cloning vector (Invitrogen), which resulted in the intermediate plasmid XXYE02.0337. The cloned DNA was confirmed by sequencing.

To replace the virE promoter in ABI strain in vivo, pMON96945 was constructed. pMON83948, which contained virE flanking sequence, was PCR-amplified with the primers Xd778 and Xd779 using pfu polymerase. The PCR product was digested with ApaI/SpeI and ligated with the Xd775 and Xd777 amplified PCR fragment from the intermediate vector XXYE02.0337 digested with the same enzymes. The resultant plasmid pMON96945 (FIG. 5) was confirmed by sequencing.

Xd778:
(SEQ ID NO: 12)
5' GGactagtCAGAAATTACGATTTTCCTAGTGCCTTC 3'

Xd779:
(SEQ ID NO: 13)
5' ATGCCAATAGgggcccAATATCGGCATTTTCTTTTGCGTTTTTATTT
G 3'

To replace the native virE operon promoter in *A. tumefaciens* ABI strain (a C58 derivative) with the identified strong constitutive P-rrn promoter, pMON96945 was electroporated into the *Agrobacterium* competent cells and selected on carbenicillin 50 mg/l for integration of P-rrn promoter by homologous recombination. The carbenicillin resistant colonies was shaken at 28° C. for 2-3 hours and plated onto LB medium with 5% sucrose for the 2nd crossover. The carbenicillin sensitive colonies were checked for the replacement of the P-rrn-virE by PCR using the following junction primers:

(SEQ ID NO: 14)
5' GGTCTGTTTTTTGACAATTGAATATGAGAAG 3'
(P-rrn 5') Xd837

(SEQ ID NO: 15)
5' GAGTCGGGCTTCCGTGCATGTTG 3'
(virE2 mid reverse) Xd838

(SEQ ID NO: 16)
5' AATGCACGGTGATGATGTTGATCG 3'
(virE upstream flanking) Xd839

-continued

```
                                            (SEQ ID NO: 17)
5' TGATCACCATggCtTTGTTTCTCC 3'
   (P-rrn-virE1 3'reverse) Xd840
```

The primers Xd839 and Xd838 amplified a 970 bp fragment from the modified ABI strain and primers Xd839 and Xd838 amplified a 759 bp fragment from the unmodified ABI strain. The modified strain was designated as AB8. The P-rrn-virE operon was constructed using pMON96945 knockout plasmid. The replacement of the virE operon promoter was confirmed by sequencing the PCR product. Other C58 derived strains with different improvements can be made using the same strategy. Over expression of the virE operon has been found is known to be useful in transferring large DNA segments to a host cell.

Example 2

Construction of P-rrn-aadA Prokaryotic Expression Cassette for Improving Growth of Bacteria Carrying Low Copy Plasmids in *Agrobacterium*

The oriRi vectors (US20070074314) grow slower than oriV vectors under antibiotic selection due to the gene dose effect of the low or multiple copy vectors in *Agrobacterium*. To construct a high expressing aadA cassette, the P-rrn with virE RBS was re-amplified with the primers Xd1021 and Xd776 using pfu polymerase and pMON96945 as a template.

```
Xd1021:
                                            (SEQ ID NO: 18)
5' GGactagtcatgaGGTCTGTTTTTTGACAATTGAATATGAGAAG 3'

Xd776:
                                            (SEQ ID NO: 19)
5' CGCATTTAGCTTGATGATCACCATggCtTTGTTTCTCCTTCAATCAT

TGACTATTGTCACGTTATTCTG 3'
```

The amplified PCR product was digested with BspHI and NcoI (underlined in primers), gel purified, and ligated into pMON83934 digested with BspHI. The ligation mixture was electroporated into *A. tumefaciens* ABI competent cells, plated onto LB medium with 100 mg/l spectinomycin and cultured at 30° C. After 2 days large colonies was transferred into LB medium containing 50 mg/l spectinomycin and shaken at 30° C. overnight. The resultant plasmid pMON107330 was rescued into *E. coli* cells, mini-prepared, and confirmed by sequencing.

A 2T-DNA vector pMON107336 was made by replacing the native bacterial spectinomycin selection cassette of 2T vector pMON107333 (opened with SpeI blunted/BspHI) with the P-rrn-aadA cassette from pMON107330 excised with PstI blunted/BspHI.

Both pMON107330 (1T oriRi) and pMON107336 (2T oriRi) contained the long version of P-rrn promoter shown in FIG. 2. Due to a HindIII site present in the P-rrn promoter, which is frequently used as restriction site for subcloning, the long version of P-rrn from pMON107330 was re-amplified with Xd1033 and Xd1034 to remove HindIII using the primers Xd1033 and Xd1034. The PCR fragment was digested with BspHI/NcoI, gel purified, and inserted into pMON83934 (US20070074314) opened with BspHI, which resulted in the 1 T-DNA vector pMON107331. The short version P-rrn in pMON107331 (1T oriRi) is shown in FIG. 3.

```
Xd1033:
                                            (SEQ ID NO: 20)
5' GATTTTGGtcatgaGCGGGACCTGGAGAGATTTGGGTCCTAGTG 3'

Xd1034:
                                            (SEQ ID NO: 9)
5' aggcatgcaagcttGATGGGGATCAGATTGTCGTTTCC 3'
```

Example 3

Testing the Chimeric P-rrn Promoter Function in *E. coli*

Figure 10:
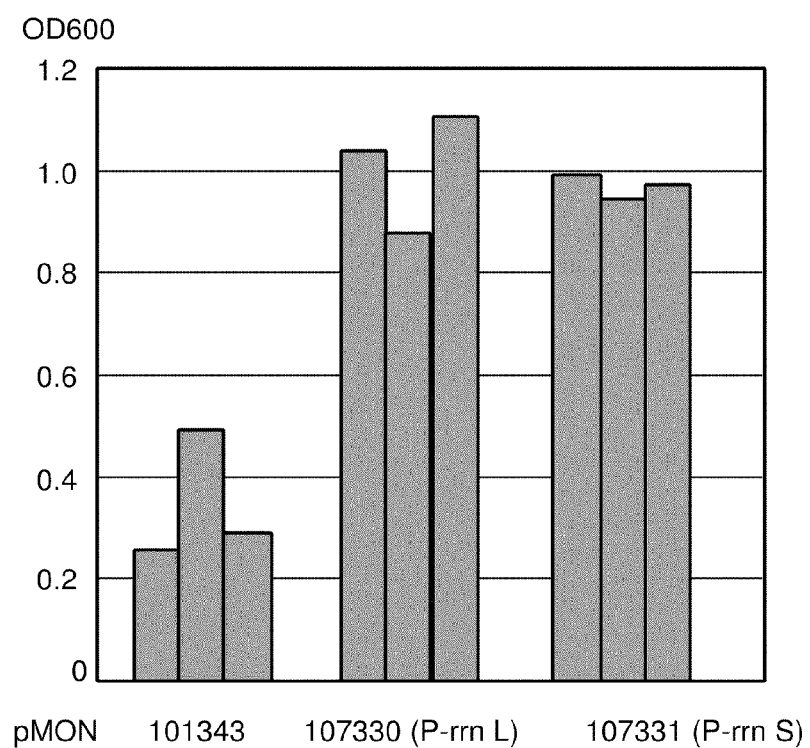
FIG. 10. Growth rates of *E. coli* TOP10 cells carrying vectors comprising P-rrn-aadA expression cassette. pMON101343 with oriV replication origin for *Agrobacterium* replication and aadA with native aadA promoter, pMON107330 with oriRi replication origin for *Agrobacterium* replication with long P-rrn-aadA (P-rrn L), and pMON107331 with oriRi replication origin for *Agrobacterium* replication with short P-rrn-aadA (P-rrn S).

Plasmids carrying long or short versions of P-rrn and the aadA gene were introduced into *E. coli* TOP10 by electroporation and selected on LB medium containing 50 mg/l spectinomycin. The *E. coli* colonies were picked and grown in LB containing 100 mg/l spectinomycin. As seen in the FIG. 10, growth rates for *E. coli* carrying either longer or shorter version of P-rrn with aadA were higher than the construct carrying the aadA gene with its own promoter. It took less than 5 hours at the spectinomycin concentration of 50 mg/l or 6 hours at spectinomycin concentration of 100 mg/l to grow *E. coli* cells to a desirable level. The time savings indicated that the cloning process could be improved using these sequences. The growth rate of *E. coli* with the P-rrn-aadA cassettes was significantly faster that the native aadA cassette at 100 mg/l spectinomycin, indicating that the P-rrn-aadA is more highly expressed than the native cassette, and provides higher protection from the antibiotic selection.

Example 4

Testing the Chimeric P-rrn Promoter Function in *Agrobacterium*

Plasmids carrying the long or the short versions of P-rrn and the aadA gene were introduced into *Agrobacterium* ABI by electroporation and selected on LB medium containing 50 mg/l spectinomycin. Three colonies were inoculated into 3 ml LB with various spectinomycin concentrations as shown in FIG. 11, and cultures were shaken at 250 rpm at 28° for 17 hours after which absorbance was measured at OD600.

Figure 11:
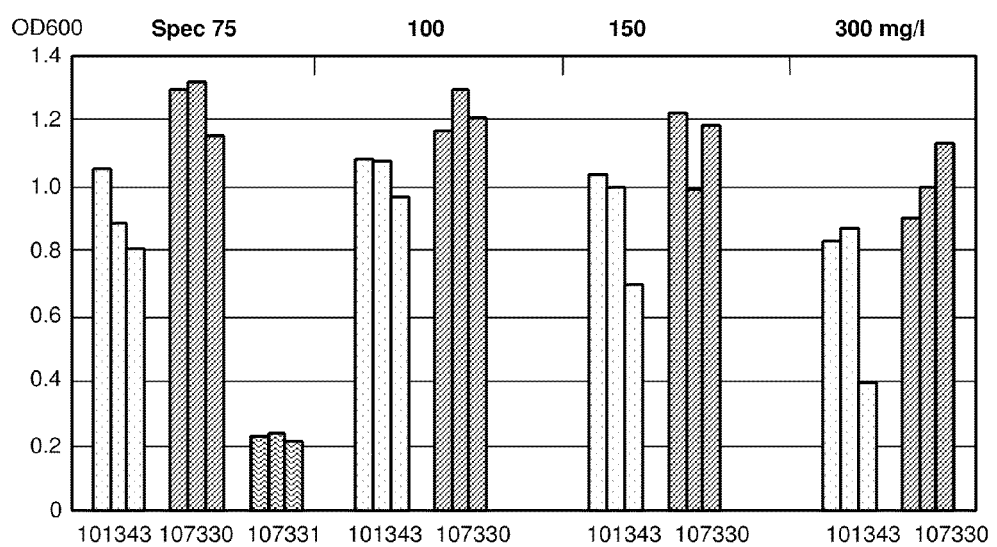
FIG. 11. Growth rates of *Agrobacterium tumefaciens* ABI cells carrying vectors comprising P-rrn-aadA expression cassettes. pMON101343 with oriV replication origin for *Agrobacterium* replication and aadA with its native aadA promoter, pMON107330 with oriRi replication origin for *Agrobacterium* replication with long P-rrn-aadA (P-rrn L), and pMON107331 with oriRi replication origin for *Agrobacterium* replication with short P-rrn-aadA (P-rrn S).

As shown in FIG. 11, when the constructs carrying chimeric P-rrn-aadA cassettes were transferred into *Agrobacterium* and *Agrobacterium* was grown, it was surprisingly found that *Agrobacterium* carrying the pMON107331 construct containing the short P-rrn promoter with aadA showed significantly reduced growth. This may indicate that requirements for promoter strength are different in *E. coli* and *Agrobacterium*. The presence of a cis enhancer element or additional *Agrobacterium*-specific regulatory sequences located in the 51 bp upstream of the HindIII in the P-rrn was also found.

The oriRi vector with the long version of P-rrn resist a wide range of spectinomycin and grows fairly well at 300 mg/l spectinomycin, while the wild type aadA cassette in an oriRi vector (See U.S. Patent Application Publication 2007/0074314, incorporated herein by reference) showed significant growth reduction at spec 75 mg/l. Although the oriRi vectors replicated in *Agrobacterium* as 1-2 copies per chromosome and the oriV vector replicates at approximately 10 copies per chromosome, the *Agrobacterium* growth rate with oriRi vectors was 0.1-0.2 OD better than the oriV vector in all spectinomycin concentrations tested. Since the spectinomycin resistance level showed a linear relationship with plasmid copy number (U.S. Patent Application Publication 2007/0074314), it was estimated that the P-rrn promoter strength is at least 10 times stronger than the native aadA promoter.

Example 5

Figure 12:
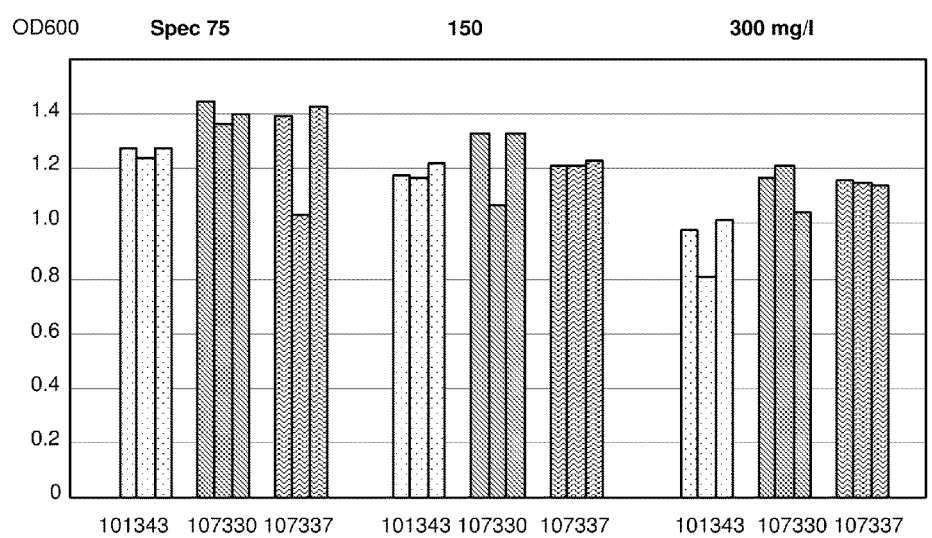
FIG. 12. Growth rates of *Agrobacterium tumefaciens* ABI cells carrying vectors comprising P-rrn-aadA expression cassettes. pMON101343 with oriV replication origin for *Agrobacterium* replication and aadA with its native aadA promoter, pMON107330 with oriRi replication origin for *Agrobacterium* replication with long P-rrn-aadA (P-rrn L), and pMON107337 with oriRi replication origin for *Agrobacterium* replication with long P-rrn-aadA (P-rrn L) with filled-in HindIII site.

Deletion of HindIII Site from the P-rrn Promoter Retains the Full P-rrn Activity Since 51 bp upstream of HindIII site were responsible for high expression of P-rrn in *Agrobacterium* and because the HindIII site is useful for subcloning, the HindIII site was filled-in with T4 DNA polymerase in the long version of P-rrn to remove it (FIG. 4) as well as to retain the P-rrn promoter strength in *Agrobacterium*. For this purpose, the 2T-DNA vector pMON107336 was used since it contains only a single HindIII site. After filling-in, the vector was self-ligated and transformed into *E. coli* TOP10 cells (Invtrogen). Colonies from overnight LB plate with 50 mg/l spectinomycin were picked and cultured in 2 ml LB with 50 mg/ml spectinomycin for 5 hours. The mini-prepared plasmid was digested with HindIII/PstI to confirm the loss of HindIII site. The resulting plasmid pMON107337 was confirmed by sequencing and transferred into *Agrobacterium* to test the spectinomycin resistance level as described above. It was confirmed that the HindIII minus P-rrn promoter has the same level of spectinomycin resistance as shown in FIG. 12.

The 51 bp HindIII upstream fragment is conserved in *A. tumefaciens* as found by the alignment of the consensus P-rrn sequence from C58 and MAFF301001 strains. This indicates that the 51 bp fragment is useful for enhanced function in *Agrobacterium* cells.

Example 6

Identification of P-rrn Sequences from Other Rhizobiales

P-rrn promoters from a number of bacteria belonging to the Rhizobiales and Rhizobiaceae were identified by aligning operons/genes for 16s rRNAs available in the public databases. The accession numbers for these are as follows: *Agrobacterium tumefaciens* C58 (Genbank accessions AE009201, AE008688; AE008980, AE008688; AE009324, AE008689; AE009348, AE008689), *Rhizobium leguminosarum* bv. *viciae* 3841 (complete genome; Genbank accession NC_008380), *Rhizobium etli* CFN 42 (complete genome; Genbank accession NC_007761), *Sinorhizobium medicae* WSM419 (Genbank accession CP000738), and *Sinorhizobium meliloti* 1021 (Genbank accession NC_003047). The identified P-rrn promoters from each bacteria and the consensus sequences are provided as SEQ ID NOs: 1-5 and 22-37 (see description of sequence listing). Alignment of consensus sequences of all P-rrn promoters from these organisms showed about 70% identity. Each P-rrn promoter is operably linked to a RBS sequence which is operably linked to a transcribable sequence to produce an expression unit/cassette which is then inserted in a vector as described elsewhere in the specification. The vector is then transformed into a host cell to enhance the expression of the transcribable sequence in the host cell.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

I claim:

1. A polynucleotide molecule comprising a 16S rDNA promoter molecule operably linked to a nucleic acid comprising a heterologous ribosomal binding site, wherein the polynucleotide molecule has promoter activity, and wherein the 16S rDNA promoter molecule is isolated from a prokaryote, wherein the polynucleotide comprises a sequence selected from the group consisting of:
   a) a nucleic acid sequence comprising SEQ ID NO:7;
   b) a nucleic acid sequence comprising at least 85% sequence identity to SEQ ID NO:7; and
   c) a fragment of the nucleic acid sequence of SEQ ID NO:7.

2. The polynucleotide molecule of claim 1, wherein the polynucleotide comprises at least 90%, at least 95% identity, or at least 98% identity to the nucleic acid sequence of SEQ ID NO:7.

3. The polynucleotide molecule of claim 1, comprising the sequence of SEQ ID NO:7.

4. The polynucleotide molecule of claim 1, comprising a fragment of the nucleic acid sequence of SEQ ID NO:7.

5. A polynucleotide molecule comprising a 16S rDNA promoter molecule operably linked to a nucleic acid comprising a heterologous ribosomal binding site, wherein the polynucleotide molecule has promoter activity, and wherein the 16S rDNA promoter molecule is isolated from a prokaryote, wherein the ribosomal binding site is isolated from the Agrobacterium virE operon.

* * * * *

SEQUENCE LISTING

<160> NUMBER OF SEQ ID NOS: 37

<210> SEQ ID NO 1
<211> LENGTH: 290
<212> TYPE: DNA
<213> ORGANISM: Agrobacterium tumefaciens C58

<400> SEQUENCE: 1

```
gaagtggtct gttttttgac aattgaatat gagaagaaag agaaacgtgg gcggcgaagc      60
ttgcgggacc tggagagatt tgggtcctag tgaatagact ttgacggtca cgtttttaatg     120 agacaacacc aatttcgcga gcagagatgc ttgttgagat tgatgtgagt tctcgtcgat     180
tcagaataac gtgacaatag tcaatgattg aattctcaac ttgagagttt gatcctggct     240
cagaacgaac gctggcggca ggcttaacac atgcaagtcg aacgccccgc                290
```

<210> SEQ ID NO 2
<211> LENGTH: 300
<212> TYPE: DNA
<213> ORGANISM: Agrobacterium tumefaciens C58

<400> SEQUENCE: 2

```
ttcggagttt gattatttga ctgctttgaa gtggtctgtt ttttgacaat tgaatatgag      60
aagaaagaga aacgtgggcg gcgaagcttg cgggacctgg agagatttgg gtcctagtga     120
```

```
atagactttg acggtcacgt tttaatgaga caacaccaat ttcgcgagca gagatgcttg      180
ttgagattga tgtgagttct cgtcgattca gaataacgtg acaatagtca atgattgaat      240
tctcaacttg agagtttgat cctggctcag aacgaacgct ggcggcaggc ttaacacatg      300

<210> SEQ ID NO 3
<211> LENGTH: 360
<212> TYPE: DNA
<213> ORGANISM: Agrobacterium tumefaciens C58

<400> SEQUENCE: 3
gattatttga ctgctttgaa gtggtctgtt ttttgacaat tgaatatgag aagaaagaga       60
aacgtgggcg gcgaagcttg cggggtctgg agcaattcag gtcctagtga atagactttg      120
acggtcacgt tttaatgaga caacaccaat ttcgcgggca gcgatgttcg ttgagattga      180
tgtgagttct cgtcgattca gaataacgtg acaatagtca atgattgaat tctcaacttg      240
agagtttgat cctggctcag aacgaacgct ggcggcaggc ttaacacatg caagtcgaac      300
gccccgcaag gggagtggca gacgggtgag taacgcgtgg gaatctaccc atctctgcgg      360

<210> SEQ ID NO 4
<211> LENGTH: 320
<212> TYPE: DNA
<213> ORGANISM: Agrobacterium tumefaciens C58

<400> SEQUENCE: 4
gcttttagct ttgggggttt gattttgtga ctgcattgag cggtctgttt tttgacaatt       60
gaatatgaga agaaagagaa acgtgggcgg cgaagcttgc gggacctgga gagatttggg      120
tcctagtgaa tagactttga cggtcacgtt ttaatgagac aacaccaatt tcgcgagcag      180
agatgtttgt tgagattgat gtgagttctc gtcgattcag aataacgtga caatagtcaa      240
tgattgaatt ctcaacttga gagtttgatc ctggctcaga acgaacgctg gcggcaggct      300
taacacatgc aagtcgaacg                                                  320

<210> SEQ ID NO 5
<211> LENGTH: 207
<212> TYPE: DNA
<213> ORGANISM: Artificial Sequence
<220> FEATURE:
<223> OTHER INFORMATION: Synthetic Sequence

<400> SEQUENCE: 5
ggtctgtttt ttgacaattg aatatgagaa gaaagagaaa cgtgggcggc gaagcttgcg       60
ggacctggag agatttgggt cctagtgaat agactttgac ggtcacgttt taatgagaca      120
acaccaattt cgcgagcaga gatgcttgtt gagattgatg tgagttctcg tcgattcaga      180
ataacgtgac aatagtcaat gattgaa                                          207

<210> SEQ ID NO 6
<211> LENGTH: 224
<212> TYPE: DNA
<213> ORGANISM: Artificial Sequence
<220> FEATURE:
<223> OTHER INFORMATION: Synthetic Sequence

<400> SEQUENCE: 6
ggtctgtttt ttgacaattg aatatgagaa gaaagagaaa cgtgggcggc gaagcttgcg       60
ggacctggag agatttgggt cctagtgaat agactttgac ggtcacgttt taatgagaca      120
acaccaattt cgcgagcaga gatgcttgtt gagattgatg tgagttctcg tcgattcaga      180
```

```
ataacgtgac aatagtcaat gattgaagga gaaacaaagc catg            224

<210> SEQ ID NO 7
<211> LENGTH: 167
<212> TYPE: DNA
<213> ORGANISM: Artificial Sequence
<220> FEATURE:
<223> OTHER INFORMATION: Synthetic sequence

<400> SEQUENCE: 7
gcgggacctg gagagatttg ggtcctagtg aatagacttt gacggtcacg ttttaatgag   60
acaacaccaa tttcgcgagc agagatgctt gttgagattg atgtgagttc tcgtcgattc  120
agaataacgt gacaatagtc aatgattgaa ggagaaacaa agccatg                167

<210> SEQ ID NO 8
<211> LENGTH: 227
<212> TYPE: DNA
<213> ORGANISM: Artificial Sequence
<220> FEATURE:
<223> OTHER INFORMATION: Synthetic sequence

<400> SEQUENCE: 8
gtctgttttt tgacaattga atatgagaag aaagagaaac gtgggcggcg aagctagctt   60
gcgggacctg gagagatttg ggtcctagtg aatagacttt gacggtcacg ttttaatgag  120
acaacaccaa tttcgcgagc agagatgctt gttgagattg atgtgagttc tcgtcgattc  180
agaataacgt gacaatagtc aatgattgaa ggagaaacaa agccatg                227

<210> SEQ ID NO 9
<211> LENGTH: 39
<212> TYPE: DNA
<213> ORGANISM: Artificial Sequence
<220> FEATURE:
<223> OTHER INFORMATION: Synthetic primer

<400> SEQUENCE: 9
ggactagtgg tctgtttttt gacaattgaa tatgagaag                          39

<210> SEQ ID NO 10
<211> LENGTH: 69
<212> TYPE: DNA
<213> ORGANISM: Artificial Sequence
<220> FEATURE:
<223> OTHER INFORMATION: Synthetic primer

<400> SEQUENCE: 10
cgcatttagc ttgatgatca ccatggcttt gtttctcctt caatcattga ctattgtcac   60
gttattctg                                                           69

<210> SEQ ID NO 11
<211> LENGTH: 38
<212> TYPE: DNA
<213> ORGANISM: Artificial Sequence
<220> FEATURE:
<223> OTHER INFORMATION: Synthetic primer

<400> SEQUENCE: 11
cgggcccaca cttgaatcgg taatttcatt ctaaagtg                           38

<210> SEQ ID NO 12
<211> LENGTH: 36
<212> TYPE: DNA
<213> ORGANISM: Artificial Sequence
```

```
<220> FEATURE:
<223> OTHER INFORMATION: Synthetic primer

<400> SEQUENCE: 12
ggactagtca gaaattacga ttttcctagt gccttc                              36

<210> SEQ ID NO 13
<211> LENGTH: 48
<212> TYPE: DNA
<213> ORGANISM: Artificial Sequence
<220> FEATURE:
<223> OTHER INFORMATION: Synthetic primer

<400> SEQUENCE: 13
atgccaatag gggcccaata tcggcatttt cttttgcgtt tttatttg                 48

<210> SEQ ID NO 14
<211> LENGTH: 31
<212> TYPE: DNA
<213> ORGANISM: Artificial Sequence
<220> FEATURE:
<223> OTHER INFORMATION: Synthetic primer

<400> SEQUENCE: 14
ggtctgtttt ttgacaattg aatatgagaa g                                   31

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
gagtcgggct tccgtgcatg ttg                                            23

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
aatgcacggt gatgatgttg atcg                                           24

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
tgatcaccat ggctttgttt ctcc                                           24

<210> SEQ ID NO 18
<211> LENGTH: 44
<212> TYPE: DNA
<213> ORGANISM: Artificial Sequence
<220> FEATURE:
<223> OTHER INFORMATION: Synthetic primer

<400> SEQUENCE: 18
ggactagtca tgaggtctgt tttttgacaa ttgaatatga gaag                     44
```

```
<210> SEQ ID NO 19
<211> LENGTH: 69
<212> TYPE: DNA
<213> ORGANISM: Artificial Sequence
<220> FEATURE:
<223> OTHER INFORMATION: Synthetic primer

<400> SEQUENCE: 19
cgcatttagc ttgatgatca ccatggcttt gtttctcctt caatcattga ctattgtcac    60
gttattctg                                                            69

<210> SEQ ID NO 20
<211> LENGTH: 44
<212> TYPE: DNA
<213> ORGANISM: Artificial Sequence
<220> FEATURE:
<223> OTHER INFORMATION: Synthetic primer

<400> SEQUENCE: 20
gattttggtc atgagcggga cctggagaga tttgggtcct agtg                     44

<210> SEQ ID NO 21
<211> LENGTH: 38
<212> TYPE: DNA
<213> ORGANISM: Artificial Sequence
<220> FEATURE:
<223> OTHER INFORMATION: Synthetic primer

<400> SEQUENCE: 21
aggcatgcaa gcttgatggg gatcagattg tcgtttcc                            38

<210> SEQ ID NO 22
<211> LENGTH: 426
<212> TYPE: DNA
<213> ORGANISM: Rhizobium leguminosarum bv. viciae

<400> SEQUENCE: 22
gttgggtgtg ttgactgttc taatgggtta gttctataag cccactcact gaacgagggc    60
ggcggcgctg ctggcgacga agtctttcgt tctagtgaaa ctcaagcgga ttggcgattg   120
ctggtttgtg ttctgggcgc gagtttggag cgggttttgt cgacgacgtt ttggtgtcgt   180
ctgttatttg acaattgaat attgtgaaga aagagaaacg tgggcggcgg agcttgcggg   240
atctgaagag atttggatcc tttgaaagag actttgacgg tcacgtttat caagagaagt   300
tacactggtt ttcggagatt gagtttaggc ttagttccct ggaaaacagg tgtgaagttc   360
tcgtcgattc aaagaacgtg atttagtcga gattgaattc tcaacatgag agtttgatcc   420
tggctc                                                             426

<210> SEQ ID NO 23
<211> LENGTH: 660
<212> TYPE: DNA
<213> ORGANISM: Rhizobium leguminosarum bv. viciae

<400> SEQUENCE: 23
cctccgttaa ccataatttc gcgcaagatc ctgttttctc gctatctttc ggtcgttgag    60
aacgatgttc cgatggattt ttgaccaggt ggtaaaggaa ttttcggaaa tccgtcccga   120
aagggcgccc tgtggataag atccatcgat aaaaatgcca gccgaatcaa cctgttacaa   180
aaatgtcaaa aaactttggt tgggtgtgtt gactgttcta atgggttagt tctataagcc   240
cactcactga acgagggcgg cggcgctgct ggcgacgaag tctttcgttc tagtgaaact   300
caagcggatt ggcgattgct ggtttgtgtt ctgggcgcga gtttggagcg ggttttgtcg   360
```

```
acgacgtttt ggtgtcgtct gttatttgac aattgaatat tgtgaagaaa gagaaacgtg    420
ggcggcggag cttgcgggat ctgaagagat ttggatcctt tgaaagagac tttgacggtc    480
acgtttatca agagaagtta cactggtttt cggagattga gtttaggctt agtttcctgg    540
aaaacaggtg tgaagttctc gtcgattcaa agaacgtgat ttagtcgaga ttgaattctc    600
aacatgagag tttgatcctg gctcagaacg aacgctggcg gcaggcttaa cacatgcaag    660
```

<210> SEQ ID NO 24
<211> LENGTH: 540
<212> TYPE: DNA
<213> ORGANISM: Rhizobium leguminosarum bv. viciae

<400> SEQUENCE: 24

```
tgcaaggccg gtcggaatcc gggaaacgaa cgcatttgcg tgctgtctgg aattttttcct    60 gtaaaaacaa tatcttgaaa gaaaaatcaa ttttttcgaa aagcgctgtt gactgttcta   120
atgggttagt tctataagcc cactcactga acgagggcgg cggcgctgct ggcgacgaag   180
tctttcgttc tagtgaaact caagcggatt ggcgattgct ggtttgtgtt ctgggcgcga   240
gtttggagcg ggttttgtcg acgacgtttt ggtgtcgtct gttatttgac aattgaatat   300
tgtgaagaaa gagaaacgtg ggcggcggag cttgcgggat ctgaagagat ttggatcctt   360
tgaaagagac tttgacggtc acgtttatca agagaagtta cactggtttt cggagattga   420
gtttaggctt agtttcctgg aaaacaggtg tgaagttctc gtcgattcaa agaacgtgat   480
ttagtcgaga ttgaattctc aacatgagag tttgatcctg gctcagaacg aacgctggcg   540
```

<210> SEQ ID NO 25
<211> LENGTH: 397
<212> TYPE: DNA
<213> ORGANISM: Rhizobium leguminosarum bv. viciae

<400> SEQUENCE: 25

```
tgactgttct aatgggttag ttctataagc ccactcactg aacgagggcg gcggcgctgc    60
tggcgacgaa gtctttcgtt ctagtgaaac tcaagcggat ggcgattgc tggtttgtgt   120 tctgggcgcg agtttggagc gggttttgtc gacgacgttt tggtgtcgtc tgttatttga   180
caattgaata ttgtgaagaa agagaaacgt gggcggcgga gcttgcggga tctgaagaga   240
tttggatcct ttgaaagaga ctttgacggt cacgtttatc aagagaagtt acactggttt   300
tcggagattg agtttaggct tagtttcctg gaaaacaggt gtgaagttct cgtcgattca   360
aagaacgtga tttagtcgag attgaattct caacatg                            397
```

<210> SEQ ID NO 26
<211> LENGTH: 480
<212> TYPE: DNA
<213> ORGANISM: Rhizobium etli

<400> SEQUENCE: 26

```
aacccttaat tttcagcctg ttacaaaaat gtcaaaaaac ttttgttatg gctgttgact    60
tagaaaaggg gttggttcta taagcccact cactgaacga gggcggcggc gctgctggcg   120
acgaagtctc tcgctctgaa gaaactcaag cggattggca gatgctggtt tgtgttctgg   180
gcgcaagttt ggaacgggtt ttggtgacgg cttttggtcg tcggttattt gacaattgaa   240
gaatggaaga aagagaaacg tgggcggcg agcttgcggg accggcagag atgctggttc   300
tttgaaagag actttggcgg tcacgtttat caagagaata cacctcattt tgagcgcagt   360
gatgcgcttt cgagatgggt gtgagttctc gtcgattcag acgtgacgta atgccaatga   420
```

```
ttgaattctc aacatgagag tttgatcctg gctcagaacg aacgctggcg gcaggcttaa      480
```

<210> SEQ ID NO 27
<211> LENGTH: 600
<212> TYPE: DNA
<213> ORGANISM: Rhizobium etli

<400> SEQUENCE: 27

```
tttgctcaaa gcgctgtttt cacgcgatct ttcgccgcct ggggatggca attcgaggac       60
tttttgacca gctgataaag aaatattcgg aaatatgtcg cgaaaacgcc gcctgtggat      120
aaggcatgcg aagaaaataa cagccgaatc agcctgttac aaaaatgtca aaaactttt      180
gttatggctg ttgacttaga aaggggttg gttctataag cccactcact gaacgagggc      240
ggcggcgctg ctggcgacga agtctctcgc tctgaagaaa ctcaagcgga ttggcagatg      300
ctggtttggt tctgggcgca agtttggaac gggttttggt gacggctttt ggtcgtcggt      360
tatttgacaa ttgaagaatg gaagaaagag aaacgtgggc ggcggagctt gcgggaccgg      420
cagagatgct ggttctttga aagagacttt ggcggtcacg tttatcaaga gaatacacct      480
cattttgagc gcagtgatgc gctttcgaga tgggtgtgag ttctcgtcga ttcagacgtg      540
acgtaatgcc aatgattgaa ttctcaacat gagagtttga tcctggctca gaacgaacgc      600
```

<210> SEQ ID NO 28
<211> LENGTH: 600
<212> TYPE: DNA
<213> ORGANISM: Rhizobium etli

<400> SEQUENCE: 28

```
gattgtgatc atgtcggggc gcgtgagacg aaagagcgtt ctttcccacg gaaagtcgaa       60
gaatgttcac ttctcttgct ctgtcaggcc ggtcgaatcc ggaaaacgac cgcacctaag      120
ggatgtccgg aatgtcggta gtaaaaacaa tggcttggaa gaaaaatgat tttttttcgaa     180
aagcgctgtt gacttagaaa aggggttggt tctataagcc cactcactga acgagggcgg      240
cggcgctgct ggcgacgaag tctctcgctc tgaagaaact caagcggatt ggcagatgct      300
ggtttgtgtt ctgggcgcaa gtttggaacg ggttttggtg acggcttttg gtcgtcggtt      360
atttgacaat tgaagaatgg aagaaagaga acgtgggcg gcggagcttg cgggaccggc       420
agagatgctg gttctttgaa agagactttg gcggtcacgt ttatcaagag aatacacctc      480
attttgagcg cagtgatgcg ctttcgagat gggtgtgagt tctcgtcgat tcagacgtga      540
cgtaatgcca atgattgaat tctcaacatg agagtttgat cctggctcag aacgaacgct      600
```

<210> SEQ ID NO 29
<211> LENGTH: 430
<212> TYPE: DNA
<213> ORGANISM: Rhizobium etli

<400> SEQUENCE: 29

```
aacccttaat tttcagcctg ttacaaaaat gtcaaaaaac ttttgttatg gctgttgact       60
tagaaaaggg gttggttcta taagcccact cactgaacga gggcggcggc gctgctggcg      120
acgaagtctc tcgctctgaa gaaactcaag cggattggca gatgctggtt tgtgttctgg      180
gcgcaagttt ggaacgggtt ttggtgacgg cttttggtcg tcggttattt gacaattgaa      240
gaatggaaga agagaaacg tggcggcgg agcttgcggg accggcagag atgctggttc       300
tttgaaagag actttggcgg tcacgtttat caagagaata cacctcattt tgagcgcagt      360
gatgcgcttt cgagatgggt gtgagttctc gtcgattcag acgtgacgta atgccaatga      420
```
ttgaattctc                                                            430

<210> SEQ ID NO 30
<211> LENGTH: 540
<212> TYPE: DNA
<213> ORGANISM: Sinorhizobium medicae

<400> SEQUENCE: 30
gaaggcgaaa ttgtgtatcc acagcccgag agattccctc ggaaaagaat ctgcgacccg      60
caaaagcttg ctctccgggg gtttgtcaga aaactgtcat ttttttttgaa gaaccctgtt    120 gacgtgccgg agtgggtggg tctataagcc cgatcactga cgagggcggc ggcgctgctg    180
gcgacgatgc ctttcgctct agggtttcct tgattggcgg atgctgattt tgggggttggg    240 actttcgggt tttggccttt aggggactgt tgacggggat ttcactcgtc tgttttttga    300
caattgaata tagagaaaga gaaacgtggg cggcggagct tgcgggaccct gaagagattt    360 gggttctgga aagagacttt ggcggtcacg ttttgacaag agactacacc agtcttctcg    420
gggttttggc cttgattgaa gatgggtgtg tgttctcgtc aattaagtcg acgtgattta    480
tgccaatgat tgaattctca acttgagagt ttgatcctgg ctcagaacga acgctggcgg    540

<210> SEQ ID NO 31
<211> LENGTH: 600
<212> TYPE: DNA
<213> ORGANISM: Sinorhizobium medicae

<400> SEQUENCE: 31
ataggtcgtt aaccatatag gaccggcagg cacggacttt cctgggcgcg agcgctcaaa      60
aaaacgatcg ccactctgcc cggtttcgga tcagttcgcg gccgaaagaa taattccttc    120
aaaaacagcc acttacgatt ttctcgtaat tttttgaaat tggttgttga ctggggaaag    180
ggctggggtc tataagcccg atcactgacg agggcggcgg cgctgctggc gacgatgccc    240
ttcgctctag ggtttccttg attggcggat gctgattttg gggttgggac tttcgggttt    300 tggccttttag gggactgttg acggggattt cactcgtctg ttttttgaca attgaatata    360
gagaaagaga aacgtgggcg gcggagcttg cgggacctga agagatttgg gttctggaaa    420
gagactttgg cggtcacgtt ttgacaagag actacaccag tcttctcggg gttttggcct    480
tgattgaaga tgggtgtgtg ttctcgtcaa ttaagtcgac gtgatttatg ccaatgattg    540
aattctcaac ttgagagttt gatcctggct cagaacgaac gctggcggca ggcttaacac    600

<210> SEQ ID NO 32
<211> LENGTH: 600
<212> TYPE: DNA
<213> ORGANISM: Sinorhizobium medicae

<400> SEQUENCE: 32
cgcacggccc cttgaaaagc ggggctgcgt taaccatata gacctcaatc cccggaagcg      60
ccgaaagtcc gtaaagcgga cccgaattgg tagaggcttt ggacgacttt tcgcgccaac    120
gaaaataacc attcaaaaac agccacttac gattttctcg taattttttg aaattggttg    180
ttgactgggg aaagggctgg ggtctataag cccgatcact gacgagggcg gcagcgctgc    240
tggcgacgat gcctttcgct ctagggtttc cttgattggc ggatgctgat tttggggttg    300 ggacttttcgg gttttggcct ttagggggact gttgacgggg atttcactcg tctgtttttt    360
gacaattgaa tatagagaaa gagaaacgtg ggcggcggag cttgcgggac ctgaagagat    420
ttgggttctg gaaagagact ttggcggtca cgttttgaca agagactaca ccagtcttct    480

```
cggggttttg gccttgattg aagatgggtg tgtgttctcg tcaattaagt cgacgtgatt    540
tatgccaatg attgaattct caacttgaga gtttgatcct ggctcagaac gaacgctggc    600

<210> SEQ ID NO 33
<211> LENGTH: 567
<212> TYPE: DNA
<213> ORGANISM: Sinorhizobium medicae

<400> SEQUENCE: 33
cgcacggccc cttgaaaagc ggggctgcgt taaccatata gacctcaatc cccggaagcg     60
ccgaaagtcc gtaaagcgga cccgaattgg tagaggcttt ggacgacttt tcgcgccaac    120
gaaaataacc attcaaaaac agccacttac gattttctcg taattttttg aaattggttg    180
ttgactgggg aaagggctgg ggtctataag cccgatcact gacgagggcg gcagcgctgc    240
tggcgacgat gcctttcgct ctagggtttc cttgattggc ggatgctgat tttgggggttg    300 ggactttcgg gttttggcct ttaggggact gttgacgggg atttcactcg tctgtttttt    360
gacaattgaa tatagagaaa gagaaacgtg ggcggcggag cttgcgggac ctgaagagat    420
ttgggttctg gaaagagact ttggcggtca cgttttgaca agagactaca ccagtcttct    480
cggggttttg gccttgattg aagatgggtg tgtgttctcg tcaattaagt cgacgtgatt    540
tatgccaatg attgaattct caacttg                                        567

<210> SEQ ID NO 34
<211> LENGTH: 543
<212> TYPE: DNA
<213> ORGANISM: Sinorhizobium meliloti

<400> SEQUENCE: 34
tctcatcccc agaagcgccg aaagcccgca aagcggaccc gtattggtag cagcgtcgga     60 cgtctttcg cgtgctttgg aaatggcccc ttaaaaacag tcacttacga ttttctgctg    120 atttttttgaa atcgttgtt gacgtgttgg agggctgggg tctataagcc cgatcactga    180
cgagggcggc ggcgctgctg gcgacgatgt ccttcgctct agggtttcca agattagcgg    240
atgctgattg tcgggactgg gcctttgagg ttttggtctt gttggaatgt cgacgggatt    300
gtttctcgtc tgtttttga caattgaata tagagaaaga gaaacgtggg cggcggagct    360
cgcgggacct gaagagattt gggttctgga aagagacttt ggcggtcacg ttttgacaag    420
agactaacac cagttttctc ggttcgggct tcggttcggg ctgattgaag atgggtgtga    480
gttctcgtcg attcaaagtc aacgtgattt aagccaatga ttgaattctc aacttgagag    540
ttt                                                                  543

<210> SEQ ID NO 35
<211> LENGTH: 594
<212> TYPE: DNA
<213> ORGANISM: Sinorhizobium meliloti

<400> SEQUENCE: 35
tcgcagcgca gggcaggccc cgacgccgcg cctccggaac gaagcggcga tgatctgggt     60
tagatcggtc gattgtgaag aagtgagggc gaaattatgt atccacaggc tgagggagcg    120
gctcgaaaaa gaatctgcga cccgcaaaac cctgcttttc cggctttgt cagaaaactg    180 tcatttttttt tgaagaagcc tgttgacgtg ttggagggct ggggtctata agcccgatca    240
ctgacgaggg cggcggcgct gctggcgacg atgtccttcg ctctagggtt tccaagatta    300
gcggatgctg attgtcggga ctgggccttt gaggttttgg tcttgttgga atgtcgacgg    360
```

```
gattgtttct cgtctgtttt ttgacaattg aatatagaga aagagaaacg tgggcggcgg    420
agctcgcggg acctgaagag atttgggttc tggaaagaga ctttggcggt cacgttttga    480
caagagacta acaccagttt tctcggttcg ggcttcggtt cgggctgatt gaagatgggt    540
gtgagttctc gtcgattcaa agtcaacgtg atttaagcca atgattgaat tctc          594

<210> SEQ ID NO 36
<211> LENGTH: 660
<212> TYPE: DNA
<213> ORGANISM: Sinorhizobium meliloti

<400> SEQUENCE: 36
ggatgcaaga ataaacacct ttaaaaacag tcacttacga ttttctgctg attttttgaa     60
aatcgttgtt gacgtgttgg agggctgggg tctataagcc cgatcactga cgagggcggc    120
ggcgctgctg gcgacgatgt ccttcgctct agggtttcca agattagcgg atgctgattg    180
tcgggactgg gcctttgagg ttttggtctt gttggaatgt cgacgggatt gtttctcgtc    240
tgttttttga caattgaata tagagaaaga gaaacgtggg cggcggagct cgcgggacct    300
gaagagattt gggttctgga aagagacttt ggcggtcacg ttttgacaag agactaacac    360
cagttttctc ggttcgggct tcggttcggg ctgattgaag atgggtgtga gttctcgtcg    420
attcaaagtc aacgtgattt aagccaatga ttgaattctc aacttgagag tttgatcctg    480
gctcagaacg aacgctggcg gcaggcttaa cacatgcaag tcgagcgccc cgcaagggga    540
gcggcagacg ggtgagtaac gcgtgggaat ctacccttt ctacggaata acgcagggaa    600
acttgtgcta ataccgtatg agcccttcgg gggaaagatt tatcgggaaa ggatgagccc    660

<210> SEQ ID NO 37
<211> LENGTH: 386
<212> TYPE: DNA
<213> ORGANISM: Sinorhizobium meliloti

<400> SEQUENCE: 37
tgttggaggg ctggggtcta taagcccgat cactgacgag ggcggcggcg ctgctggcga     60
cgatgtcctt cgctctaggg tttccaagat tagcggatgc tgattgtcgg gactgggcct    120
ttgaggtttt ggtcttgttg aatgtcgac gggattgttt ctcgtctgtt ttttgacaat    180
tgaatataga gaaagagaaa cgtgggcggc ggagctcgcg gacctgaag agatttgggt    240 tctggaaaga gactttggcg gtcacgtttt gacaagagac taacaccagt tttctcggtt    300
cgggcttcgg ttcgggctga ttgaagatgg gtgtgagttc tcgtcgattc aaagtcaacg    360
tgatttaagc caatgattga attctc                                         386
```